United States Patent [19]
Breu et al.

[11] Patent Number: 5,420,129
[45] Date of Patent: May 30, 1995

[54] PHENYLSULFONYLAMIDE PYRIMIDINE

[75] Inventors: Volker Breu, Schliengen, Germany; Kaspar Burri, Binningen, Switzerland; Jean-Marie Cassal, Mulhouse, France; Martine Clozel, St. Louis, France; Georges Hirth, Huningue, France; Bernd-Michael Löffler, Oberrimsingen, Germany; Marcel Müller, Frenkenforf, Switzerland; Werner Neidhart, Bartenheim, France; Henri Ramuz, Birsfelden, Switzerland

[73] Assignee: Hoffmann-La Roche Inc., Nutley, N.J.

[21] Appl. No.: 164,167

[22] Filed: Dec. 8, 1993

[30] Foreign Application Priority Data

Dec. 10, 1992 [CH] Switzerland .................. 3777/92
Dec. 11, 1992 [CH] Switzerland .................. 3799/92
Oct. 14, 1993 [CH] Switzerland .................. 3114/93

[51] Int. Cl.⁶ ............................................. A61K 31/50
[52] U.S. Cl. ................................. 514/252; 514/231.2; 514/231.5; 514/253; 514/256; 514/257; 544/295; 544/296; 544/238; 544/309; 544/311; 544/317; 544/319; 544/327
[58] Field of Search ............. 554/117; 514/252, 231.2, 514/231.5, 253, 256, 257; 544/239, 295, 296, 309, 311, 317, 319, 327

[56] References Cited

U.S. PATENT DOCUMENTS 5,270,313 12/1993 Burri et al. .................... 514/252

OTHER PUBLICATIONS

Gruendemann et al., Chemical Abstracts, vol. 108:94000y, pp. 606–607 (1988).
Much et al., Chemical Abstracts, vol. 104:95587z, p. 455 (1986).

*Primary Examiner*—José G. Dees
*Assistant Examiner*—Deborah D. Carr

*Attorney, Agent, or Firm*—George M. Gould; George W. Johnston; Robert A. Silverman

[57] ABSTRACT

The invention is concerned with novel sulphonamides and their use as medicaments. In particular, the invention is concerned with compounds of the formula

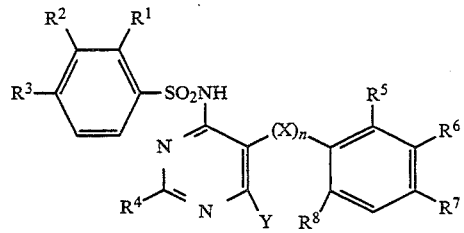

wherein
$R^1$ is hydrogen, lower-alkyl, lower-alkoxy, lower-alkylthio, halogen or trifluoromethyl;
$R^2$ is hydrogen, lower-alkyl, halogen, lower-alkoxy, trifluoromethyl or —OCH$_2$COOR$^9$;
$R^3$ is hydrogen, lower-alkyl, halogen, lower-alkylthio, trifluoromethyl, lower-alkoxy or trifluoromethoxy;
$R^2$ and $R^3$ together are butadienyl, methylenedioxy, ethylene-dioxy or isopropylidenedioxy;
$R^4$ is hydrogen, lower-alkyl, trifluoromethyl, lower-alkoxy, lower-alkylthio, hydroxy-lower-alkyl, hydroxy-lower-alkoxy, hydroxy-lower-alkoxy-lower-alkyl, hydroxy-lower-alkoxy-lower-alkoxy, alkoxy-lower-alkyl, alkoxy-lower-alkyloxy, lower-alkylsulfinyl, lower-alkylsulfonyl, 2-methoxy-3-hydroxypropoxy, 2-hydroxy-3-phenylpropyl, amino-lower-alkyl, lower-alkylamino-lower-alkyl, di-lower-alkylamino-lower-alkyl, amino, lower-alkylamino, di-lower-alkylamino, arylamino, aryl, arylthio, aryloxy, aryl-lower-alkyl, heterocyclyl, heterocyclo-lower-alkyl, heterocyclylamino, heterocyclylthio, heterocyclyloxy, —CHO, —CH$_2$OH or —CH$_2$Cl;
$R^5$ to $R^8$ are independently hydrogen, halogen, trifluoromethyl, lower-alkoxy, lower-alkylthio or cyano;
$R^6$ and $R^5$ or $R^7$ together are butadienyl, methylenedioxy, ethylenedioxy or isopropylidenedioxy;
X is —O— or —S—;

(Abstract continued on next page.)

Y is —CHO, $C_{1-4}$-alkyl, —$(CH_2)_{1-4}$—Z—$R^9$, —$(CH_2)_{1-4}$—OC(O)$(CH_2)_{1-4}CH_3$, —$(CH_2)_{1-4}$OC(O)Het, —$(CH_2)_{1-4}$NHC(O)$R^{10}$, —$(CH_2)_{1-4}OCH_2$CH(OH)$CH_2$OH and cyclic ketals thereof, —$(CH_2)_{1-4}NR^9CH_2$CH(OH)$CH_2$OH, —$(CH_2)_{1-4}OCH_2CH_2SCH_3$, —$(CH_2)_{1-4}OCH_2CH_2S(O)CH_3$, —$(CH_2)_{1-4}O(CH_2)_{1-4}$—Z H, —$(CH_2)_{1-4}O(CH_2)_{1-4}OC(O)R^{10}$, —$(CH_2)_{1-4}NR^9(CH_2)_{1-4}Z$ H, —$(CH_2)_{1-4}O(CH_2)_{1-4}OC(O)$Het, —$(CH_2)_{0-3}$CH(OH)$R^{10}$, —$(CH_2)_{0-3}$CH(OH)$(CH_2)_{1-4}Z$ H, —$(CH_2)_{0-3}$CH(OH)$CH_2SCH_3$, —$(CH_2)_{0-3}$CH(OH)$CH_2S(O)CH_3$, —$(CH_2)_{0-3}$CH(OH)$OCH_2CH_2$OH, —$(CH_2)_{0-3}$C(O)$(CH_2)_{1-4}CH_3$, —$(CH_2)_{0-3}$C(O)$(CH_2)_{1-4}Z$ $R^{11}$, —$(CH_2)_{0-3}$C(O)$CH_2$Hal, —$(CH_2)_{1-4}$Hal, —$(CH_2)_{1-4}$CN, —$(CH_2)_{0-3}$C(O)$OR^9$, —$OR^{12}$ or —$SR^{12}$;

$R^9$ is hydrogen or $C_{1-4}$-alkyl;

$R^{10}$ is $C_{1-4}$-alkyl;

$R^{11}$ is hydrogen, $C_{1-4}$-alkanoyl or heterocyclylcarbonyl;

$R^{12}$ is $C_{1-4}$-alkyl or —$(CH_2)_{0-4}$-aryl;

Z is —O—, —S— or —$NR^9$—;

Het is a heterocyclic residue;

Hal is halogen; and n is 0 or 1; and salts thereof.

14 Claims, No Drawings

PHENYLSULFONYLAMIDE PYRIMIDINE

SUMMARY OF THE INVENTION

The invention is concerned with novel sulphonamides and their use as medicaments. In particular, the invention is concerned with compounds of the formula

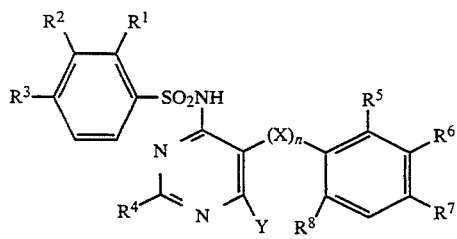

wherein
$R^1$ is hydrogen, lower-alkyl, lower-alkoxy, lower-alkylthio, halogen or trifluoromethyl;
$R^2$ is hydrogen, lower-alkyl, halogen, lower-alkoxy, trifluoromethyl or —$OCH_2COOR^9$;
$R^3$ is hydrogen, lower-alkyl, halogen, lower-alkylthio, trifluoromethyl, lower-alkoxy or trifluoromethoxy;
$R^2$ and $R^3$ together are butadienyl, methylenedioxy, ethylene-dioxy or isopropylidenedioxy;
$R^4$ is hydrogen, lower-alkyl, trifluoromethyl, lower-alkoxy, lower-alkylthio, hydroxy-lower-alkyl, hydroxy-lower-alkoxy, hydroxy-lower-alkoxy-lower-alkyl, hydroxy-lower-alkoxy-lower-alkoxy, alkoxy-lower-alkyl, alkoxy-lower-alkyloxy, lower-alkylsulfinyl, lower-alkylsulfonyl, 2-methoxy-3-hydroxypropoxy, 2-hydroxy-3-phenylpropyl, amino-lower-alkyl, lower-alkylamino-lower-alkyl, di-lower-alkylamino-lower-alkyl, amino, lower-alkylamino, di-lower-alkylamino, arylamino, aryl, arylthio, aryloxy, aryl-lower-alkyl, heterocyclyl, heterocyclyl-lower-alkyl, heterocyclylamino, heterocyclylthio, heterocyclyloxy, —CHO, —$CH_2OH$ or —$CH_2Cl$;
$R^5$ to $R^8$ are independently hydrogen, halogen, trifluoromethyl, lower-alkoxy, lower-alkylthio or cyano;
$R^6$ and $R^5$ or $R^7$ together are butadienyl, methylenedioxy, ethylenedioxy or isopropylidenedioxy;
X is —O— or —S—;
Y is —CHO, $C_{1-4}$-alkyl, —$(CH_2)_{1-4}$—Z—$R_9$, —$(CH_2)_{1-4}$—OC(O)$(CH_2)_{1-4}CH_3$, —$(CH_2)_{1-4}$OC(O)Het, —$(CH_2)_{1-4}$NHC(O)$R^{10}$, —$(CH_2)_{1-4}$O$CH_2$CH(OH)$CH_2OH$ and cyclic ketals thereof, —$(CH_2)_{1-4}NR^9CH_2CH(OH)CH_2OH$, —$(CH_2)_{1-4}OCH_2CH_2SCH_3$, —$(CH_2)_{1-4}OCH_2CH_2S(O)CH_3$, —$(CH_2)_{1-4}O(CH_2)_{1-4}$—Z H, —$(CH_2)_{1-4}O(CH_2)_{1-4}OC(O)R^{10}$, —$(CH_2)_{1-4}NR^9(CH_2)_{1-4}Z$ H, —$(CH_2)_{1-4}O(CH_2)_{1-4}OC(O)$Het, —$(CH_2)_{0-3}CH(OH)R^{10}$, —$(CH_2)_{0-3}CH(OH)(CH_2)_{1-4}Z$ H, —$(CH_2)_{0-3}CH(OH)CH_2SCH_3$, —$(CH_2)_{0-3}CH(OH)CH_2S(O)CH_3$, —$(CH_2)_{0-3}CH(OH)OCH_2CH_2OH$, —$(CH_2)_{0-3}C(O)(CH_2)_{1-4}CH_3$, —$(CH_2)_{0-3}C(O)(CH_2)_{1-4}Z R^{11}$, —$(CH_2)_{0-3}C(O)CH_2Hal$, —$(CH_2)_{1-4}Hal$, —$(CH_2)_{1-4}CN$, —$(CH_2)_{0-3}C(O)OR^9$, —$OR^{12}$ or —$SR^{12}$;
$R^9$ is hydrogen or $C_{1-4}$-alkyl;
$R^{10}$ is $C_{1-4}$-alkyl;
$R^{11}$ is hydrogen, $C_{1-4}$-alkanoyl or heterocyclylcarbonyl;
$R^{12}$ is $C_{1-4}$-alkyl or —$(CH_2)_{0-4}$-aryl;
Z is —O—, —S— or —$NR^9$—;

Het is a heterocyclic residue;
Hal is halogen; and
n is 0 or 1; and salts thereof.

The compounds of formula I are inhibitors of endothelin receptors. They can accordingly be used for the treatment of disorders which are associated with endothelin activities, especially circulatory disorders such as hypertension, ischaemia, vasospasms and angina pectoris.

DETAILED DESCRIPTION OF THE INVENTION

The invention is concerned with compounds of the formula

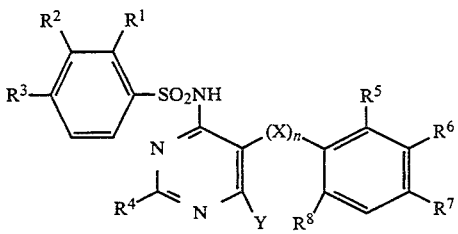

wherein
$R^1$ is hydrogen, lower-alkyl, lower-alkoxy, lower-alkylthio, halogen or trifluoromethyl;
$R^2$ is hydrogen, lower-alkyl, halogen, lower-alkoxy, trifluoromethyl or —$OCH_2COOR_9$;
$R^3$ is hydrogen, lower-alkyl, halogen, lower-alkylthio, trifluoromethyl, lower-alkoxy or trifluoromethoxy;
$R^2$ and $R^3$ together are butadienyl, methylenedioxy, ethylene-dioxy or isopropylidenedioxy;
$R^4$ is hydrogen, lower-alkyl, trifluoromethyl, lower-alkoxy, lower-alkylthio, hydroxy-lower-alkyl, hydroxy-lower-alkoxy, hydroxy-lower-alkoxy-lower-alkyl, hydroxy-lower-alkoxy-lower-alkoxy, alkoxy-lower-alkyl, alkoxy-lower-alkyloxy, lower-alkylsulfinyl, lower-alkylsulfonyl, 2-methoxy-3-hydroxypropoxy, 2-hydroxy-3-phenylpropyl, amino-lower-alkyl, lower-alkylamino-lower-alkyl, di-lower-alkylamino-lower-alkyl, di-lower-alkylamino-lower-alkyl, amino, lower-alkylamino, di-lower-alkylamino, arylamino, aryl, arylthio, aryloxy, aryl-lower-alkyl, heterocyclyl, heterocyclyl-lower-alkyl, heterocyclylamino, heterocyclylthio, heterocyclyloxy,— CHO,—$CH_2OH$ or —$CH_2Cl$;
$R^5$ to $R^8$ are independently hydrogen, halogen, trifluoromethyl, lower-alkoxy, lower-alkylthio or cyano;
$R^6$ and $R^5$ or $R^7$ together are butadienyl, methylenedioxy, ethylenedioxy or isopropylidenedioxy;
X is —O—or —S—;
Y is —CHO, $C_{1-4}$-alkyl, —$(CH_2)_{1-4}$—Z—$R^9$, —$(CH_2)_{1-4}$—OC(O)$(CH_2)_{1-4}CH_3$, —$(CH_2)_{1-4}$OC(O)Het, —$(CH_2)_{1-4}$NHC(O)$R^{10}$, —$(CH_2)_{1-4}$O$CH_2$CH(OH)$CH_2OH$ and cyclic ketals thereof, —$(CH_2)_{1-4}NR^9CH_2CH(OH)CH_2OH$, —$(CH_2)_{1-4}OCH_2CH_2SCH_3$, —$(CH_2)_{1-4}OCH_2CH_2S(O)CH_3$, —$(CH_2)_{1-4}O(CH_2)_{1-4}$—Z H, —$(CH_2)_{1-4}O(CH_2)_{1-4}OC(O)R^{10}$, —$(CH_2)_{1-4}NR^9(CH_2)_{1-4}Z$ H, —$(CH_2)_{1-4}O(CH_2)_{1-4}OC(O)$Het, —$(CH_2)_{0-3}CH(OH)R^{10}$, —$(CH_2)_{0-3}CH(OH)(CH_2)_{1-4}Z$ H, —$(CH_2)_{0-3}CH(OH)CH_2SCH_3$, —$(CH_2)_{0-3}CH(OH)CH_2S(O)CH_3$, —$(CH_2)_{0-3}C(O)(CH_2)_{1-4}CH_3$, —$(CH_2)_{0-3}C(O)(CH_2)_{1-4}Z R^{11}$, —$(CH_2)_{0-3}C(O)CH_2Hal$, —$(CH_2$ )$_{1-4}$Hal, —(CH$_2$)$_{1-4}$CN, —(CH$_2$)$_{0-3}$C(O)OR$^9$, —OR$^{12}$ or —SR$_{12}$;

R$^9$ is hydrogen or C$_{1-4}$-alkyl;

R$^{10}$ is C$_{1-4}$-alkyl;

R$^{11}$ is hydrogen, C$_{1-4}$-alkanoyl or heterocyclylcarbonyl;

R$^{12}$ is C$_{1-4}$-alkyl or —(CH$_2$)$_{0-4}$-aryl;

Z is —O—, —S— or —NR$^9$—;

Het is a heterocyclic residue;

Hal is halogen; and n is 0 or 1; and salts thereof.

The term "lower" denotes groups with 1-7 C atoms, preferably 1-4 C atoms. Alkyl, alkoxy and alkylthio groups as well as alkyl groups as components of alkanoyl groups can be straight-chain or branched. Methyl, ethyl, propyl, isopropyl, butyl, sec. and tert.butyl are examples of such alkyl groups. Halogen denotes fluorine, chlorine, bromine and iodine, with chlorine being preferred. Examples of aryl residues are phenyl and substituted phenyl residues, with especially halogen, lower-alkyl, lower-alkoxy, carboxyl and trifluoromethyl coming into consideration as substituents. Examples of heterocyclyl residues are mono- or bicyclic 5- and 6-membered heterocyclic residues which are mono- or di-substituted, for example, by lower-alkyl, lower-alkoxy, halogen, aryl or aryl-lower-alkyl, or unsubstituted and which have oxygen, nitrogen or sulphur as the hetero atom, such as 2- and 3-furyl, 2-,4- and 5-pyrimidinyl, 2-, 3- and 4-pyridyl and pyridyl-N-oxide, 1,2- and 1,4-diazinyl, morpholino, 2- and 3-thienyl, isoxazolyl, oxazolyl, thiazolyl, imidazolyl, pyrrolyl, benzofuranyl, benzothienyl, indolyl, purinyl, quinolyl, isoquinolyl and quinazolyl. Examples of salts are alkali salts such as Na and K salts and alkaline earth metal salts such as Ca and Mg salts.

A preferred group of compounds within formula I comprises those in which n=1 and X is —O— and, furthermore, those in which R$^6$ signifies lower-alkoxy, especially methoxy; R$^5$ and R$^7$ is hydrogen and R$^8$ signifies halogen, especially chlorine.

Preferred substituents R$^1$ and R$^2$ are hydrogen, preferred substituents R$^3$ are lower-alkyl, especially tert.butyl. Preferred substituents R$^4$ are hydrogen, 2-pyrimidinyl, 2- and 3-furyl, 2- and 3-thienyl, p-methoxyphenyl and, especially morpholino.

Preferred substituents Y are CHO, C$_{1-4}$-alkyl, —(CH$_2$)$_{1-4}$—Z$^l$—R$^9$, —(CH$_2$)1-4NHC(O)R$_{10}$, —CH$_2$OCH$_2$CH(OH)CH$_2$OH and cyclic ketals thereof, —CH$_2$NR$^9$CH$_2$CH(OH)CH$_2$OH, —CH$_2$OCH$_2$CH$_2$S(O)CH$_3$, —CH$_2$O(CH$_2$)$_{1-4}$—Z H, —CH$_2$O(CH$_2$)$_{1-4}$OC(O)R$^{10}$, —CH$_2$O(CH$_2$)$_{1-4}$OC(O)Het or—CH$_2$Hal, especially hydroxymethyl, 2-hydroxy-ethoxymethyl and 2,3-dihydroxypropoxymethyl.

The compounds of formula I can be manufactured by reacting a compound of the formula a) reacting a compound of the formula:

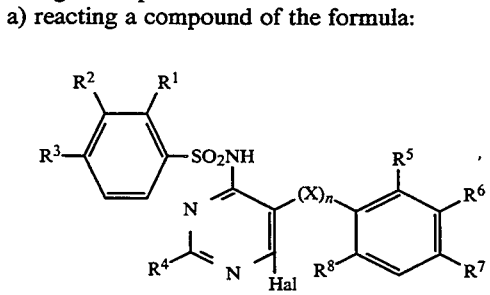

II wherein R$^1$-R$^8$, X, and n have the significance given above and Hal is halogen, with a compound of the formula

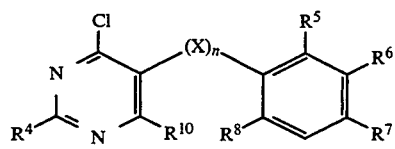

III wherein A is oxygen or sulphur and M is an alkali metal, to give a compound of formula I in which Y is the residue —OR$^{12}$ or —SR$^{12}$; or b) reacting a compound of the formula:

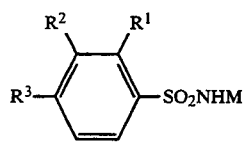

IV wherein R$^4$-R$^8$, R$^{10}$, X and n have the significance given above, with a compound of the formula

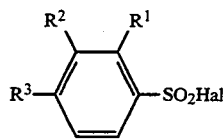

V wherein R$^1$, R$^2$ and R$^3$ and M have the significance given above, to give a compound of formula I in which Y is a residue R$^{10}$ and R$^1$-R$^8$, X and n have the significance given above, if desired, oxidizing a compound of formula I obtained in which Y and/or R$^4$ is a residue CH$^3$ to give a compound of formula I in which Y and- /or R$^4$ is a residue CHO and, if desired, converting the residue CHO into a different residue Y defined above and/or R$^4$; or c) reacting a compound of the formula

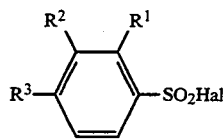

VI wherein R$^1$, R$^2$, R$^3$ and Hal have the significance given above, with a compound of the formula

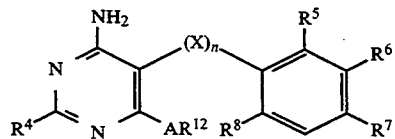

VII wherein R$^4$—R$^8$, R$^{12}$, n, A and X have the significance given above; and, if desired, converting the compound of formula I obtained into a salt.

The reaction of a compound of formula II with a compound of formula III is conveniently carried out using the (thio)alcohol corresponding to the compound III, that is to say, for example, in ethanol when A is oxygen and R$^{12}$ is ethyl. The alkali metal M is preferably sodium. The reaction is conveniently carried out while heating, for example, to 40°-120° C.

The reaction of the compounds IV and VII with the compounds V and, respectively, VI can be carried out in a manner known per se for the manufacture of sulphonamides, for example, in an inert organic solvent such as dimethyl sulphoxide, conveniently while heating and in an inert gas atmosphere, for example, under argon. The alkali metal in the compounds of formula III and V is preferably Na+ or K+.

In the reaction of a compound of formula VI with a compound of formula VII, hydroxy and amino groups which may be present in the latter compound as substitutents $R^4$-$R^9$ are conveniently protected. Hydroxy groups can be protected, for example, by silyl groups such as dimethyl tert-butylsilyl groups or acyl groups such as acetyl; amino groups can be protected by tert-butoxycarbonyl or benzyloxycarbonyl. These protecting groups can be introduced in a manner known per se and can be removed after the reaction of the compounds VI and VII.

The compounds of formula I in which Y and/or $R^4$ is a residue $CH_3$, obtained as previously described, can be converted into other compounds of formula I by substituent modification. Thus, the group $CH_3$ represented by the substituents Y and/or $R^4$ can be converted into a CHO group by oxidation. The oxidation can be carried out in a manner known per se, for example, with selenium dioxide. The formyl group in the thus-obtained compound can be reduced to the hydroxymethyl group. This reduction can be accomplished in a manner known per se, using reduction agents such as $NaBH_4$. The hydroxymethyl (or alkyl) group can be converted by reaction with a halogenating agent such as $POCl_3$/$PCl_5$ into a halomethyl (or alkyl) group from which by reaction with alcohols or aminoalcohols there can be obtained compounds of formula I in which Y is a residue $-(CH_2)_{1-4}ZR^9$, $-CH_2OCH_2CH(OH)CH_2OH$ and cyclic ketals thereof, $-CH_2NR^9CH_2CH(OH)CH_2OH$ or $-CH_2O(CH_2)_{1-4}ZH$. Hydroxy or amino groups present in the thus-obtained compounds of formula I can be esterified, there being obtained compounds of formula I in which Y is one of the residues set forth above in which the residue $R^{11}$ is present in the meaning $C_{10-4}$-alkanoyl or heterocyclylcarbonyl. Alternatively, the formyl group can be converted in a Grignard reaction with alkylmagnesium halides into a compound of formula I in which Y is a residue $-CH(OH)R^{11}$. Furthermore, the formyl group can be reacted with Grignard compounds of the formula $BrMg-(CH_2)_{1-4}-Z-H$ in which OH and SH groups are present in protected form (for example, as the benzyl ether) in order to obtain (after cleavage of OH and SH protecting groups) compounds of formula I with $Y=-CH(OH)(CH_2)_{1-4}-Z-H$. By reacting a compound of formula I with dimethyl sulphide/Li there can be obtained compounds of formula I with $Y=-CH(OH)CH_2SCH_3$ which can be oxidized with $NaIO_4$ to compounds of formula I with $Y=-CH(OH)CH_2S(O)CH_3$.

Compounds of formula I with $Y=-C(O)R_{10}$ or $-C(O)(CH_2)_{1-4}-Z-R^{11}$ can be manufactured by oxidizing corresponding compounds in which Y is a residue $-CH(OH)R^{10}$ or $-CH(OH)(CH_2)_{1-4}ZR^{11}$, in which case OH or SH groups $ZR^{11}$ are conveniently intermediately protected, for example, as the benzyl ether. As the oxidation agent for this oxidation there comes into consideration for example, $CrO_3$/pyridine.

All of these reactions can be carried out in a manner known per se. Finally, the compounds of formula I can be converted into pharmaceutically acceptable salts, for example, alkali salts such as Na and K salts, in a manner known per se.

The compounds which are used as starting materials, insofar as they are not known or their preparation is described hereinafter, can be prepared analogous to known methods or to the methods described hereinafter.

Compounds of formula II in which n=1 can be obtained as illustrated in the following Formula Scheme:

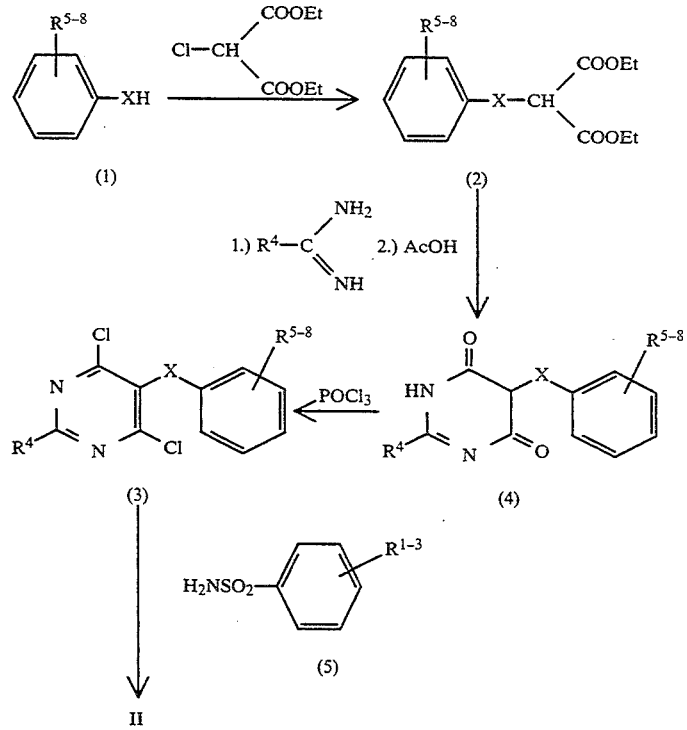

Alkylation of the phenol (or thiophenol) (1) with diethyl chloromalonate yields compound (2) which is condensed with formamidine acetate or a homologous compound such as acetamidine acetate to the pyrimidinedione derivative (3). Using phosphorus oxychloride there is obtained therefrom the dichloro compound (4) which yields compound II which n=1 upon reaction with a stoichiometric amount of compound (5). Compounds of formula II in which n=0 can be prepared analogously to the following Scheme:

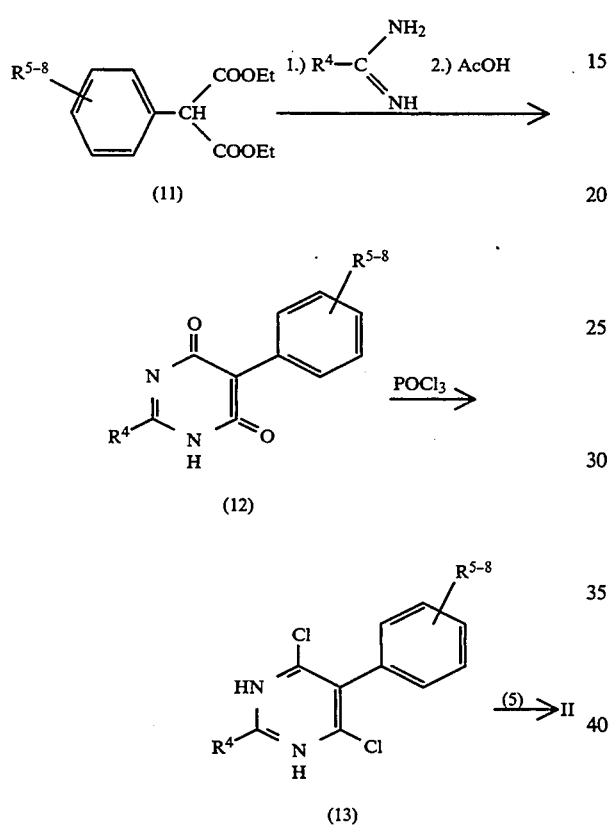

All of these reactions are standard operations and can be carried out under conditions which are usual for such reactions and which will be familiar to a person skilled in the art.

Compounds of formula IV with n=1 can be prepared as follows:

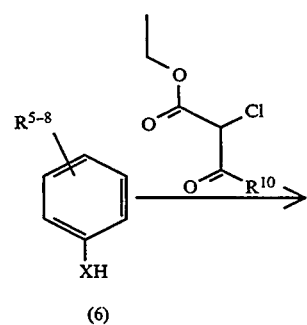

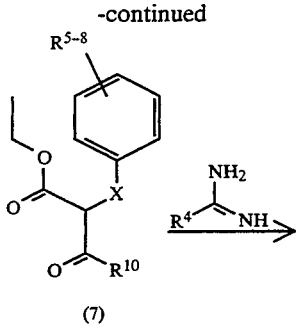

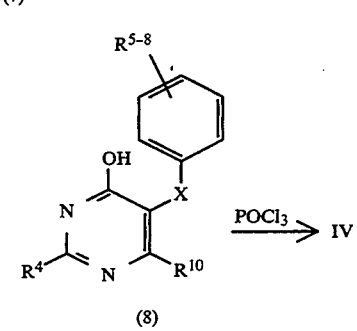

A phenol or thiophenol of formula (6) can be converted in the presence of sodium in a suitable solvent, for example, toluene, with ethyl 2-chloroacetate into a compound of formula (7) from which by condensation with the amidine R⁴C(NH)NH₂ there can be prepared the hydroxypyrimidine derivative (8) or its tautomer —NH—CO—. Replacement of the hydroxy group by chlorine using POCl₃ yields compound IV.

Compounds of formula IV in which n=0 can be prepared starting from compounds of formula (9).

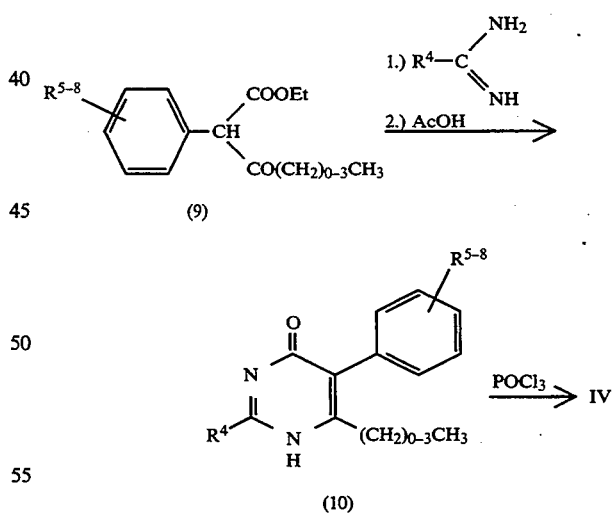

The inhibitory activity of the compounds of formula I on endothelin receptors can be demonstrated using the test procedures described hereinafter:

I. Inhibition of endothelin binding to human placenta membranes (see. Life Sci 44:1429 (1989))

Human placenta is homogenized in 5 mM Tris buffer, pH 7.4, which contains 1 mM MgCl₂ and 250 mM sucrose. The homogenizate is centrifuged at 4° C. and 3000 g for 15 minutes, the supernatant containing the plasma membrane fraction is centrifuged with 72000 g for 30 minutes and the precipitate is washed with 75 mM Tris buffer, pH 7.4, which contains 25 mM MgCl$_2$. Thereafter, precipitate obtained from in each case 10 g of original tissue is suspended in 1 ml of 75 mM Tris buffer, pH 7.4, containing 25 mM MgCl$_2$ and 250 mM sucrose, and freeze-dried at —20° C. in 1 ml aliquots.

For the binding assay, the freeze-dried membrane preparations are thawed and, after centrifugation at 20° C. and 25000 g for 10 minutes, re-suspended in assay buffer (50 mM Tris buffer, pH 7.4, containing 25 mM MnCl$_2$, 1 mM EDTA and 0.5% of bovine serum albumin). 100 μl of this membrane suspension containing 70 μg of protein are incubated with 50 μl of $^{125}$I-endothelin (specific activity 2200 Ci/mMol) in assay buffer (25000 cpm, final concentration 20 pM) and 100 μl of assay buffer containing varying concentrations of test compound. The incubation is carried out at 20° C. for 2 hours or at 4° C. for 24 hours. The separation of free and membrane-bound radioligands is carried out by filtration over a glass fiber filter.

II. Inhibition of endothelin-induced contractions in isolated rat aorta rings

Rings with a length of 5 mm were cut out from the thorax aorta of adult Wistar-Kyoto rats. The endothelium was removed by lightly rubbing the internal surface. Each ring was immersed at 37° C. in 10 ml of Krebs-Henseleit solution in an isolated bath while gassing with 95% O$_2$ and 5% CO$_2$. The isometric stretching of the rings was measured. The rings were stretched to a pre-tension of 3 g. After incubation for 10 minutes with the test compound or vehicle cumulative dosages of endothelin-1 were added. The activity of the test compound was determined by calculating the dosage ratios, i.e. the shift to the right (shift to higher values) of the EC$_{50}$ of endothelin induced by 100 μM of test compound, with EC$_{50}$ denoting the endothelin concentration required for a half-maximum contraction. The greater this dosage ratio is the more potent the test compound is in inhibiting the biological activity of en-dothelin-1. The EC$_{50}$ of endothelin in the absence of test compounds is 0.3 nM.

III. Inhibitory activity on vasoconstriction in rats

Rats were anaesthetized with Na thiobutabarbital (100 mg/kg i.p.). A catheter for measuring the systemic arterial blood pressure was placed through the femoral artery and a catheter was placed in the vena cava via the femoral vein for injection of the test compounds. A Doppler sonde was placed around the left renal artery and attached to a Doppler measuring apparatus. A renal ischaemia was produced by pinching off the left renal artery at its point of exit for 45 minutes. Ten minutes prior to the induction of the ischaemia, the test compounds were administered intraarterially (i.a.) in dosages of 5 mg/kg or intravenously (i.v.) in dosages of 10 mg/kg. In control tests the renal perfusion was reduced by 43±4% compared to the pre-ischaemic value.

The inhibitory activity of compounds of formula I determined in test procedure I is given in Table 1 as the IC$_{50}$, that as the concentration [mM] which is required to inhibit 50% of the specific binding of $^{125}$I-endothelin.

TABLE 1

| Compound of Example | IC$_{50}$ [μM] |
|---|---|
| 3 | 0.130 |
| 5 | 0.035 |

TABLE 1-continued

| Compound of Example | IC$_{50}$ [μM] |
|---|---|
| 10 | 0.184 |
| 13 | 0.182 |

On the basis of their capability of inhibiting endothelin binding, the compounds of formula I can be used as medicaments for the treatment of disorders which are associated with vasoconstriction of increasing occurrences. Examples of such disorders are high blood pressure, coronary disorders, cardiac insufficiency, renal and myocardial ischaemia, renal insufficiency, dialysis, cerebral ischaemia, cardiac infarct, migraine, subarachnoid haemorrhage, Raynaud syndrome and pulmonary high pressure. They can also be used in atherosclerosis, the prevention of restenosis after balloon-induced vascular dilation, inflammations, gastric and duodenal ulcers, ulcus cruris, gram-negative sepsis, shock, glomerulonephtritis, renal colic, glaucoma, asthma, in the therapy and prophylaxis of diabetic complications and complications in the administration of cyclosporin, as well as other disorders associated with endothelin activities.

The compounds of formula I can be administered orally, rectally, parentally, for example, intravenously, intramuscularly, subcutaneously, intrathecally or transdermally; or sublingually or as opththalmological preparations, or as an areosol. Capsules, tablets, suspensions or solutions for oral administration, suppositories, injection solutions, eye drops, salves or spray solutions are examples of administration forms.

Intravenous, intramuscular or oral administration is a preferred form of use. The dosages in which the compounds of formula I are administered in effective amounts depend on the nature of the specific active ingredient, the age and the requirements of the patient and the mode of application. In general, dosages of about 0.1–100 mg/kg in particular, 0.1–20 mg/kg body weight per day come into consideration. The pharmaceutical compositions comprising the compounds of formula I can further comprise inert or also pharmacodynamically active additives. Tablets or granulates for example, can contain a series of binders, fillers, carriers or diluents. Liquid preparations can be present, for example, in the form of a sterile water-miscible solution. Capsules can contain a filler or thickener in addition to the active ingredient. Furthermore, flavour-improving additives as well as substances usually used as preserving, stabilizing, moisture-retaining and emulsifying agents as well as salts for varying the osmotic pressure, buffers and other additives can also be present.

The previously mentioned carrier materials and diluents can comprise organic or inorganic substances, for example, water, gelatin, lactose, starch, magnesium stearate, talc, gum arabic, polyalkylene glycols and the like. It is a prerequisite that all adjuvants used in the manufacture of the pharmaceutical compositions are non-toxic.

The following Examples illustrate the invention in more detail. Of the abbreviations used therein b.p. signifies boiling point; and m.p. signifies melting point, MS signifies mass spectrum and M signifies molecular mass.

EXAMPLE 1

10.7 g of 4-[4-chloro-5-(2-chloro-5-methoxy-phenoxy)-6-methyl-pyrimidin-2-yl]-morpholine and 21.6g of p-t-butyl-benzene sulphonamide potassium in 150 ml of dry dimethyl sulphoxide were heated to 120° C. under argon for 16 hours. Thereafter, the dimethylsulphoxide was distilled off, the residue was partitioned between ethyl acetate and 1N hydrochloric acid and the organic phase was washed neutral. The organic phase was dried, the solvent was evaporated and the residue was recrystallized from dichloromethane-ethanol. There were obtained 14.7 g 4-tert-butyl-N-[5-(2-chloro-5-methoxy-phenoxy)-6-methyl-2-(morpholin-4-yl)-pyrimidin-4-yl]-benzenesulphonamide, m.p 154° C., MS: M=546.

The starting material was prepared as follows:

a) 2.8 g of sodium were added to a solution of 17.1 g of 2-chloro-5-methoxyphenol in toluene. The reaction mixture was stirred at 110° C. under argon for 3 hours and thereafter treated with a solution of 19.57 g of ethyl 2-chloroacetoacetate in toluene. The reaction mixture was stirred at 110° C. for a further 3 hours, partitioned between acetic acid-water 20% and toluene. The organic phase was dried and the solvent was distilled off. The residue was purified over silica gel with dichloromethane. There were obtained 18.2 g of ethyl (RS)-(2-chloro-5-methoxy-phenoxy)-acetoacetate as a yellowish oil. MS: M=286.

b) 0.8 g of morpholinoformamidine hydrobromide and 1 g of ethyl (RS)-(2-chloro-5-methoxy-phenoxy)-acetoacetate were added to a sodium methylate solution from 10 ml of methanol and 0.19 g of sodium. The reaction mixture was stirred at 80° C. for 16 hours, adjusted to pH 6 and concentrated. The residue is partitioned between chloroform and water. After drying and evaporation of the solvent the residue was crystallized from ethanol-dichloromethane. There was obtained 0.45g of 5-(2-chloro-5-methoxy-phenoxy)-6-methyl-2-(morpholin-4-yl)-pyrimidin-4-ol, m.p. 252° C, MS: M=351.

c) 1.72 g of 5-(2-chloro-5-methoxy-phenoxy)-6-methyl-2-(morpholin-4-yl)-pyrimidin-4-ol were mixed with 3.3 ml of POCl$_3$. The reaction mixture was stirred at 120° C. for 2 hours, thereafter the excess reagent was distilled off. The residue was taken up in chloroform and washed with water, 1N NaOH and water. The organic phase was dried, concentrated and the residue was recrystallized from ether. There were obtained 1.48 g of 4-[4-chloro-5-(2-chloro-5-methoxy-phenoxy)-6-methyl-pyrimidin-2-yl]-morpholine, m.p. 134° C., MS: M=369.

EXAMPLE 2

14.6 g of 4-tert-butyl-N-[5-(2-chloro-5-methoxy-phenoxy)-6-methyl-2-( morpholin-4-yl)-pyrimidin-4-yl]-benzenesulphonamide and 15.9 g of selenium dioxide in 500 ml of dioxan were stirred in an autoclave at 170° C. for 6 hours. The reaction mixture was filtered and the filtrate was concentrated. The residue was partitioned between chloroform and water. The organic phase was dried, the solvent was evaporated and the residue was recrystallized from dichloromethane-ethanol. There were obtained 10.3 g of 4-tert-butyl-N-[5-(2-chloro-5-methoxy-phenoxy)-6-formyl-2-(morpholin-4-yl)-pyrimidin-4-yl]-benzenesulphonamide, m.p. 235°–236° C., MS: M=561.

EXAMPLE 3

7 g of 4-tert-butyl-N-[5-(2-chloro-5-methoxy-phenoxy)-6-formyl-2-(morpholin-4-yl)-pyrimidin-4-yl]-benzenesulphonamide in 300 ml of ethanol were treated with 0.9 g of sodium borohydride. The reaction mixture was stirred at 80° C. for 1 hour. Thereafter, the ethanol was distilled off and the residue was partitioned between chloroform and 1N HCl. The organic phase was washed with water and dried, the solvent was evaporated and the residue was chromatographed over silica gel with dichloromethane. After recrystallization from dichloromethane-ethanol there were obtained 4.6 g of 4-tert-butyl-N-[5-(2-chloro-5-methoxy-phenoxy)-6-hydroxymethyl-2-(morpholin-4-yl)-pyrimidin-4-yl]-benzenesulphonamide, m.p. 103° C., MS: M=563.

EXAMPLE 4

4.57 g of 4-tert-butyl-N-[5-(2-chloro-5-methoxy-phenoxy)-6-hydroxymethyl-2-(morpholin-4-yl)-pyrimidin-4-yl]benzenesulphonamide in 50 ml of POCl$_3$ were stirred with 2.03 g of PCl$_5$ at 20° C. for 2 hours. Thereafter, the POCl$_3$ was distilled off and the residue was partitioned between ethyl acetate and aqueous 1N NaOH. The organic phase was washed with water, dried and the solvent was evaporated. The residue was chromatographed over silica gel with dichloromethane and chloroform, thereafter recrystallized from dichloromethane-ethanol. There were obtained 3.01 g of 4-tert-butyl-N-[5-(2-chloro-5-methoxy-phenoxy)-6-chloromethyl-2-(morpholin-4-yl)-pyrimidin-4-yl]-benzenesulphonamide, m.p. 170° C., MS: M=581.

EXAMPLE 5

1 g of 4-tert-butyl-N-[5-(2-chloro-5-methoxy-phenoxy)-6-chloromethyl-2-( morpholin-4-yl)-pyrimidin-4-yl]-benzenesulphonamide was added to a sodium glycolate solution from 2.5 g of ethylene glycol and 0.12 g of sodium. The reaction mixture was stirred at 80° C. under argon for 72 hours. Thereafter, the ethylene glycol was distilled off and the residue was partitioned between ethyl acetate and 1 N hydrochloric acid. The organic phase was washed with water, dried over sodium sulphate and the solvent was distilled off. The residue was chromatographed over silica gel with ether. There was obtained 0.85g of 4-tert-butyl-N-[5-(2-chloro-5methoxy-phenoxy)-6-( 2-hydroxy-ethoxymethyl)-2-( morpholin-4-yl)-pyrimidin-4-yl]-benzenesulphonamide. m.p 162°–164° C., MS: M=606.

EXAMPLE 6

As in Example 1, from 4-chloro-5-(2-chloro-5-methoxyphenoxy)-6-methyl-pyrimidine there was obtained 4-tert-butyl-N-[5-( 2-chloro-5-methoxy-phenoxy)-6-methyl-pyrimidin-4-yl]benzenesulphonamide. M.p. 191° C., MS: (M-Cl°)=426.

The starting material was prepared as follows:

As in Example 1, paragraph a), from ethyl RS)-(2-chloro-5-methoxy-phenoxy)-acetoacetate and formamidine acetate there was obtained 5-[2-chloro-5-methoxyphenoxy]-6-methyl-pyrimidin-4-ol as a wax, MS: M=266, which was reacted with POCl$_3$ in analogy to Example 1, paragraph b).

EXAMPLE 7

The compound obtained in Example 6 was converted into 4-tert-butyl-N-[5-( 2-chloro-5-methoxy-phenoxy)-6-formylpyrimidin-4-yl]-benzenesulphonamide, m.p. 99°–101° C., MS: M=475, as in Example 2.

EXAMPLE 8

4-tert-Butyl-N-[5-( 2-chloro-5-methoxy-phenoxy)-6-hydroxy-methylpyrimidin-4-yl]-benzenesulphonamide,

EXAMPLE 9

4-tert-Butyl-N-[6-chloromethyl-5-(2-chloro-5-methoxyphenoxy)-pyrimidin-4-yl]-benzenesulphonamide, m.p. 170° C., MS: (M-Cl°)=460, was obtained as in Example 4 from the compound prepared in Example 8.

EXAMPLE 10

4-tert-Butyl-N-[5-( 2-chloro-5-methoxy-phenoxy)-6-(2-hydroxy-ethoxy-methyl)-pyrimidin-4-yl]-benzenesulphonamide, m.p. 80° C., MS: (M+H)+ =522, was obtained from 4-tert-butyl-N-[6-chloromethyl-5-(2-chloro-5-methoxy-phenoxy)-pyrimidin-4-yl]benzenesulphonamide as in Example 1.

EXAMPLE 11

100 mg of 4-tert-butyl-N-[5-(2-chloro-5-methoxy-phenoxy)-6-(2-hydroxy-ethoxy-methyl)-2-(morpholin-4-yl)-pyrimidin-4-yl]benzenesulphonamide were esterified with 3-thiophenecarboxylic acid under the following conditions: 100 mg of the sulphonamide, 175 mg of N-ethyl-N'-(3-dimethylaminopropyl)-carbodiimide hydrochloride, 150 mg of triethylamine and 5 mg of dimethylaminopyridine were dissolved in 10 ml of dichloromethane and the solution was left to stand at room temperature for 2 hours. It was subsequently evaporated to dryness. The residue was azeotroped with toluene and subsequently partitioned between ethyl acetate and 1N HCI, then washed with water and isolated as usual. The compound was purified over silica gel with chloroform as the eluent. There were obtained 90 mg of thiophene-3-carboxylic acid 2-[6-( 4-tert-butylophenyl-sulphonamino )-5-( 2-chloro-5-methoxy-phenoxy)-2-(morpholin-4-yl)-pyrimidin-4-yl-methoxy]-ethyl ester, amorphous powder, MS: M=716.

EXAMPLE 12

As in Example 5, from 200 mg of 4-tert-butyl-N-[5-(2-chloro-5-methoxy-phenoxy)-6-chloromethyl-2-( morpholin-4-yl)-pyrimidin-4-yl]-benzenesulphonamide and (RS)-2,2-dimethyl-1,3-dioxolan-4-methanol Na there was obtained (RS)-4-tert-butyl-N-[5(2-chloro-5-methoxy-phenoxy)-6-(2,2-dimethyl- 1,3-dioxolan-4-ylmethoxymethyl)-2-morpholin-4-yl)-pyrimidin-4-yl]benzenesulphonamide. M.p. 155°–156° C., MS: M=676.

EXAMPLE 13

A solution of 100 mg of the compound prepared in Example 12 in 2 ml of dioxan was treated with 1.5 ml of 1N HCI and heated to 80° C. for 15 minutes. After evaporation the residue was chromatographed over silica gel with ether as the eluent and yielded 85 mg of (R,S)-4-tert-butyl-N-[5-(2-chloro-5-methoxy-phenoxy)-6-(2,3-dihydroxy-propoxymethyl)-2-(morpholin-4-yl)-pyrimidin-4yl]-benzenesulphonamide as a foam, MS: (M+H)+ =637.

EXAMPLE 14

By reacting 4-tert-butyl-N-[6-chloromethyl-5-(2-chloro-5-methoxy-phenoxy)-pyrimidin-4-yl]-benzenesulphonamide with ethanolamine there was obtained 4-tert-butyl-N-[5-(2-chloro-5-methoxy-phenoxy)-6-( 2-hydroxy-ethylaminomethyl)-pyrimidin-4yl]-benzenesulphonamide.

EXAMPLE 15

By reacting 4-tert-butyl-N-[6-chloromethyl-5-(2-chloro-5-methoxy-phenoxy)-pyrimidin-4-yl]-benzenesulphonamide with propanediol Na there was obtained 4-tert-butyl-N-[5-(2-chloro-5-methoxy-phenoxy)-6-( 3-hydroxy-propoxymethyl)-pyrimidin-4-yl]benzenesulphonamide. MS: M-(Cl°+HC(O)CH$_2$C-H$_2$OH)=436.

EXAMPLE 16

By reacting 4-tert-butyl-N-[6-chloromethyl-5-(2-chloro-5-methoxy-phenoxy)-pyrimidin-4-yl]-benzenesulphonamide with 1-aminopropandiol there was obtained (RS)-4-tert-butyl-N-[5-(2-chloro-5-methoxyphenoxy)-6-(2,3-dihydroxypropylaminomethyl)-pyrimidin-4-yl]-benzenesulphonamide. MS: (M+H)+ =551.

EXAMPLE 17

As in Example 12, from 4-tert-butyl-N-[6-chloromethyl-5-(2-chloro-5-methoxy-phenoxy)-pyrimidin-4-yl]-benzenesulphonamide there was obtained (RS)-4-tert-butyl-N-[5-(2-chloro-5-methoxyphenoxy)-6-(2,2-dimethyl-1,3-dioxolan-4-ylmethoxymethyl)-pyrimidin-4-yl]-benzenesulphonamide. MS: (M+H)+ =592.

EXAMPLE 18

As in Example 13 from (RS)-4-tert-butyl-N-[5-(2-chloro-5-methoxy-phenoxy)-6-( 2,2-dimethyl- 1,3-dioxolan-4-ylmethoxy-methyl)-pyrimidin-4-yl]-benzenesulphonamide there was obtained (RS)-4-tert-butyl-N-[5-( 2-chloro-5-methoxy-phenoxy)-6-( 2,3-dihydroxypropoxymethyl)-pyrimidin-4-yl]-benzenesulphonamide. MS: M=551.

EXAMPLE 19

By reacting 4-tert-butyl-N-[5-(2-chloro-5-methoxyphenoxy)-6-(2-hydroxy-ethoxy-methyl)-pyrimidin-4-yl]-benzenesulphonamide with nicotinic acid there was obtained pyridin-3-ylacetic acid 2-[6-(4-tert-butylphenylsulphonylamino)-5-(2-chloro-5-methoxyphenoxy)-pyrimidin-4-ylmethoxy]-ethyl ester. MS: M=626.

EXAMPLE 20

By reacting 4-tert-butyl-N-[5-(2-chloro-5-methoxyphenoxy)-6-(2-hydroxy-ethoxy-methyl)-pyrimidin-4-yl]-benzenesulphonamide with isonicotinic acid there was obtained pyridin-4-ylacetic acid 2-[6-(4-tert-butylphenylsulphonylamino)-5-(2-chloro-5-methoxyphenoxy)-pyrimidin-4-ylmethoxy]-ethyl ester.

EXAMPLE 21

By reacting 4-tert-butyl-N-[5-(2-chloro-5-methoxyphenoxy)-6-(2-hydroxy-ethoxy-methyl)-pyrimidin-4-yl]-benzenesulphonamide with 3-furancarboxylic acid there was obtained furan-3-carboxylic acid 2-[6-(4-tert-butyl-phenylsulfonylamino)-5-(2-chloro-5-methoxyphenoxy)-pyrimidin-4-ylmethoxy]-ethylester. MS: (M+H)+ =618.

EXAMPLE 22

By reacting 4-tert-butyl-N-[5-(2-chloro-5-methoxyphenoxy)-6-(2-hydroxy-ethoxy-methyl)-pyrimidin-4-yl]-benzenesuiphonamide with 3-thiophencarboxylic acid there was obtained thiophene-3-carboxylic acid m.p. 188° C., MS: M=477, was obtained as in Example 3 from the compound obtained in Example 7.

2-[6-(4-tert-butyl-phenylsulfonylamino)-5-(2-chloro-5-methoxy-phenoxy)-pyrimidin-4-ylmethoxy]-ethyl ester. MS: M=631.

EXAMPLE 23 a) As in Example 1, by reacting ethyl 2,6-dichloro-5-phenoxy-pyrimidine-4-carboxylate with p-tert.-butyl-benzene sulphonamide potassium salt there was obtained ethyl 6-(4-tert-butylphenylsulphonylamino)-2-chloro-5-phenoxy-pyrimidine-3-carboxylate. MS: (M+H+)=490.

b) The dichloride required as the starting compound may be prepared as follows: 130 mg of ethyl 2,6-dioxo-5-phenoxy-1,2,3,6-tetrahydro-pyrimidin-4-carboxylate are dissolved in 7.6 ml of POCl$_3$, treated with 7.6 mg of PCl$_5$ and the yellow solution is heated at reflux for 17 hrs. The POCl$_3$ is removed in a water-jet vacuum, the residue is partitioned between H$_2$O/ethyl acetate. After usual working up of the organic phase the residue is chromatographed on silica gel (eluent: CH$_2$Cl$_2$/ether: 6/1). There are obtained 44 mg of ethyl 2,6-dichloro-5-phenoxy-pyrimidine-4-carboxylate as an oil. MS: M=312.

c) The required starting compound may also be prepared as follows: 1.8 g of 2,6-dioxo-5-phenoxy-1,2,3,6-tetrahydro-pyrimidine-4-carboxylic acid (preparation described in: Khim Geterotsikl. Soedin., 1974, p1527) are emulsified in 65 ml of ethanol, 0.92 ml of conc. H$_2$SO$_4$ and 0.92 ml of SOCl$_2$ are subsequently added and the mixture is heated at reflux for 12 hrs. Subsequently, the mixture is concentrated on a rotary evaporator and the seperated solid is filtered off under suction and chromatographed on silica gel (eluent: CH$_2$Cl$_2$/ether: 3/1). There are obtained 520 mg of ethyl 2,6-dioxo-5-phenoxy-1,2,3,6-tetrahydro-pyrimidine-4-carboxylate as a solid. MS: M=276.

EXAMPLE 24

526 mg of 4-tert-butyl-N-[6-chloro-5-(2-methoxy-phenoxy)-2-(pyrimidin-2-yl)-pyrimidin-4-yl]-benzenesulphonamide were added to a solution of 69 mg of Na in 5.0 ml of abs. ethanol. The solution was boiled at reflux for 4 hours while stirring. After evaporating the solvent under reduced pressure the residue was partitioned between ethyl acetate and 1M aqueous tartaric acid, the organic solution was dried and evaporated and the residue was recrystallized from alcohol. There was obtained 4-tert-butyl-N-[6-ethoxy-5-(2-methoxyphenoxy)-2,2'-bipyrimidin-4-yl]benzenesulphonamide of m.p. 140°-141° C. as white crystals.

The 4-tert-butyl-N-[6-chloro-5-(2-methoxyphenoxy)-2-(pyrimidin-2-yl)-pyrimidin-4-yl]-benzenesulphonamide was prepared starting from pyrimidine-2-carboxamidine hydrochloride via rac-5-(2-methoxy-phenoxy)-2-pyrimidin-2-yl-tetrahydro-pyrimidine-4,6-dione and 4,6-dichloro-5-(2-methoxy-phenoxy)-2,2'-bipyrimidine.

EXAMPLE 25

In analogy to Example 24, from 4-tert-butyl-N-[6-chloro-5-(2-methoxy-phenoxy)-2-(pyrimidin-2-yl)-pyrimidin-4-yl]-benzenesulphonamide and sodium methylate in methanol there was obtained 4-tert-butyl-N-[6-methoxy-5-( 2-methoxy-phenoxy)-2-bipyrimidin-4-yl]-benzenesulphonamide as a solid.

EXAMPLE 26

In analogy to Example 1, from 4-chloro-5-(2-chloro-5-methoxy-phenoxy)-6-methyl-2,2'-bipyrimidinyl there was obtained 4-tert-butyl-N-[5-(2-chloro-5-methoxyphenoxy)-6-methyl-2,2'-bipyrimidinyl-4-yl]-benzenesulphonamide, m.p. 122° C., MS: (M-Cl)=504.

The starting material was prepared as follows:

(a) 5-(2-Chloro-5-methoxy-phenoxy)-6-methyl-2,2'-bipyrimidinyl-4-ol, MS: M=344, was obtained from 2-pyrimidinoamidine as in Example 1b).

(b) 4-Chloro-5-(2-chloro-5-methoxy-phenoxy)-6-methyl-2,2'-bipyrimidinyl, m.p. 110° C., MS: M=363, was obtained from the above-described substance as in Example 1c).

EXAMPLE 27

(S)-4-tert.-Butyl-N-[5-(2-chloro-5-methoxy-phenoxy)-6-(2,2-dimethyl- 1,3-dioxolan-4-yimethoxymethyl)-2-morpholin-4-yl)-pyrimidin-4-yl]-benzenesulphonamide, MS: M=677, was obtained as in Example 12.

EXAMPLE 28

(R)-4-tert.-Butyl-N-[5-(2-chloro-5-methoxy-phenoxy)-6-(2,2-dimethyl-1,3-dioxolan-4-ylmethoxymethyl)-2-(morpholin-4-yl)-pyrimidin-4-yl]-benzenesulphonamide, MS: M=677, was obtained as in Example 12.

EXAMPLE 29

(S)-4-tert.-Butyl-N-[5-( 2-chloro-4-methoxy-phenoxy)-6-(2,3-dihydroxypropoxymethyl)-2-( morpholin-4-yl)-pyrimidin-4-yl]benzenesulphonamide, MS: M=637, was prepared as in Example 13 from the compound prepared in Example 28.

EXAMPLE 30

(R)-4-tert.-Butyl-N-[5-(2-chloro-5-methoxy-phenoxy)-6(2,3-dihydroxy-propoxymethyl)-2-(morpholin-4-yl)-pyrimidin-4-yl]-benzenesulphonamide, MS: M=637, was prepared as in Example 13 from the compound prepared in Example 28.

EXAMPLE 31

(4S,5S)-4-tert.-Butyl-N-[5-(2-chloro-5-methoxy-phenoxy)-6(5-hydroxymethyl-2,2-dimethyl- 1,3-dioxolan-4-ylmethoxymethyl)-pyrimidin-4-yl]-benzenesulphonamide, MS: M=622, was obtained from 4-tert.-butyl-N-[6-chloromethyl-5-(2-chloro-5-methoxy-phenoxy)-pyrimidin-4-yl]benzenesulphonamide and 2,3—O—isopropylidene-L-threitol as in Example 17.

EXAMPLE 32

(2S ,3S )-4-tert.-Butyl-N-[5-(2-chloro-5-methoxy-phenoxy)-6-(2,3,4-trihydroxybutoxymethyl-yl]benzenesulphonamide, m.p. 192° C., MS: M=582, was obtained as in Example 18 from the compound prepared in Example 31.

EXAMPLE 33

6-( 4-tert.-Butyl-phenylsulphonamino )-5-( 2-chloro-5-methoxy-phenoxy)-2,2'-bipyrimidinyl-4-carboxaldehyde, m.p. 211° C., was obtained in analogy to Example 2 from the compound prepared as in Example 26.

EXAMPLE 34

4-tert.-Butyl-N-[5-(2-chloro-5-methoxy-phenoxy)-6-hydroxymethyl-2,2'-bipyrimidin-4-yl]-benzenesulphonamide, MS: M=556, was prepared as in Example 3 from the aldehyde prepared in Example 33.

EXAMPLE 35

4-tert.-Butyl-N-[5-(2-chloro-5-methoxy-phenoxy)-6-chloromethyl-2,2'-bipyrimidin-4-yl]-benzenesulphonamide, MS: M=574, was obtained as in Example 4 from the alcohol prepared in Example 34.

EXAMPLE 36

4-tert.-Butyl-N-[5-( 2-chloro-5-methoxy-phenoxy)-6-( 2-hydroxy-ethoxymethyl)-2-2'-bipyrimidino4-yl]benzenesulphonamide, MS: (M—H)—=598, was obtained as in Example 5 from the substance prepared in Example 35.

EXAMPLE 37

4-tert.-Butyl-N-[5-(2-chloro-5-methoxy-phenoxy)-6-methoxy-2-methyl-pyrimidin-4-yl]-benzenesulphonamide, m.p. 174° C., MS: M—(SO$_2$+Cl)=392, was prepared from 4-tert.-butyl-N[6-chloro-5-(2-chloro-5-methoxy-phenoxy)-2-methyl-pyrimidin-4yl]-benzenesulphonamide and sodium methylate in methanol as in Example 25.

EXAMPLE 38

4-tert.-Butyl-N-[5-(2-chloro-5-methoxy-phenoxy)-2-formyl-6-methoxypyrimidin-4-yl]-benzenesulphonamide, m.p. 163° C., MS: (M—H)—=503, was prepared as in Example 2 from the compound obtained as in Example 37.

EXAMPLE 39

4-tert.-Butyl-N-[5-(2-chloro-5-methoxy-phenoxy)-2-hydroxymethyl-6-methoxy-pyrimidin-4-yl]-benzenesulphonamide, m.p. 167° C., MS: M+H$^+$508, was prepared as in Example 3 from the compound obtained in Example 38.

EXAMPLE 40

4-tert.-Butyl-N-[5-(2-chloro-5-methoxy-phenoxy)-2-chloromethyl-6-methoxy-pyrimidin-4-yl]-benzenesulphonamide, m.p. 165° C., MS: M=526, was prepared as in Example 4 from the compound obtained in Example 39.

EXAMPLE 41

4-tert.-Butyl-N-[5-( 2-chloro-5-methoxy-phenoxy)-2-( 2-hydroxy-ethoxymethyl-6-methoxy-pyrimidin-4-yl]benzenesulphonamide, m.p. 150° C., MS: M=552, was prepared as in Example 5 from the compound obtained in Example 40.

EXAMPLE 42

(RS)-4-tert.-Butyl-N-[5-( 2-chloro-5-methoxyphenoxy)-2-(2,2-dimethyl- 1,3-dioxolan-4-ylmethoxymethyl)-6-methoxy-pyrimidin-4-yl]-benzenesulphonamide, m.p. 162° C., MS: M=622, was prepared as in Example 27 from the compound obtained in Example 40.

EXAMPLE 43

(RS)-4-tert.-Butyl-N-[5-(2-chloro-5-methoxy-phenoxy)-2-(2,3-dihydroxy-propoxy-methyl)-6-methoxy-pyrimidin-4-yl]benzenesulphonamide, m.p. 81° C., MS: M=582, was prepared as in Example 29 from the compound obtained in Example 42.

EXAMPLE 44

A solution of 100 mg of the compound prepared in Example 40 in 20 ml of NH3-dioxan was heated to 80° C. in a pressure flask for 16 hours. After evaporation the residue was chromatographed over silica gel with chloroform-methanol and yielded 30 mg of 4-tert.-butyl-N-[5-( 2-chloro-5-methoxy-phenoxy)-2-aminomethyl-6-methoxy-pyrimidin-4-yl]-benzenesulphonamide, MS: M=507.

EXAMPLE 45

N-[5-(2-Chloro-5-methoxy-phenoxy)-6-(2-methoxy-ethoxy)-2-methyl-pyrimidin-4-yl]-1,3-benzodioxol-5-suphonamide, m.p. 128° C., MS: M-(SO$_2$+Cl)=424, was obtained in analogy to Example 24 from N-[5-(2-chloro-5-methoxy-phenoxy)-2-methyl-6-chloro-pyrimidin-4-yl]-1,3-benzodioxol-5-sulphonamide and sodium 2methoxyethanolate.

EXAMPLE 46

N-[5-( 2-Chloro-5-methoxy-phenoxy)-2-formyl-6-(2-methoxy-ethoxy)-pyrimidin-4-yl]-1,3-benzodioxol-5-sulphonamide, MS: M(SO$_2$+Cl)=438, was prepared as in Example 2 from the compound obtained in Example 45.

EXAMPLE 47

N-[5-( 2-Chloro-5-methoxy-phenoxy)-2-hydroxymethyl-6-(2-methoxy-ethoxy)-pyrimidin-4-yl]-1,3-benzodioxol-5-sulphonamide, MS: M-(SO$_2$+Cl)=440, was prepared as in Example 3 from the compound obtained in Example 46.

EXAMPLE 48

N-[5-(2-Chloro-5-methoxy-phenoxy)-2-chloromethyl-6-(2-methoxy-ethoxy)-pyrimidin-4-yl]- 1,3-benzodioxol-5-sulphonamide, MS: M-(SO$_2$+Cl)=458, was prepared as in Example 4 from the compound obtained in Example 47.

EXAMPLE 49

N-[5-( 2-Chloro-5-methoxy-phenoxy)-2-( 2-hydroxyethoxymethyl)-6-( 2-methoxy-ethoxy)-pyrimidin-4-yl]-1,3-benzodioxol-5-sulphonamide, MS: M=584, was prepared as in Example 41 from the compound obtained in Example 48.

EXAMPLE 50

4-tert.-Butyl-N-[6-methoxy-5-(2-methoxy-phenylsulphanyl)-2-methyl-pyrimidin-4-yl]-benzenesulphonamide, MS: M=474, was obtained as in Example 25 from 4-tert.-butyl-N-[6-(2-chloro-5-methoxy-phenylsulphanyl)-2-methyl-pyrimidin-4-yl]benzenesulphonamide.

The starting material was prepared as follows:
a) 1 g of KOH was added to a solution of 2.2 ml of 2-methoxythiophenol in 30 ml of ethanol. The reaction mixture was treated at room temperature with a solution of dimethyl chloromalonate in 5 ml of ethanol, stirred for 1 hour and evaporated. The residue was partitioned between ether and water. The organic phase was dried, concentrated and the residue was purified over silica gel with methylene chloride. 3.6 g of dimethyl (2-methoxy-phenylsulphanyl)malonate, MS: M=270, were obtained.

b) 6-Hydroxy-5-(2-methoxy-phenylsulphanyl)-2-methyl-3,4-dihydro-pyrimidin-4-one, m.p. 290° C., MS: M=264, was obtained as in Example 1b from the substance prepared in Example 50a and acetamidine hydrochloride.

c) 4,6-Dichloro-5-(2-methoxy-phenylsulphanyl)-2-methylpyrimidine, m.p. 140° C., MS: M=301, was obtained as in Example 1c from the substance prepared in Example 50b.

d) 4-tert.-Butyl-N-[6-chloro-5-(2-methoxy-phenylsulphanyl)-2-methyl-pyrimidin-4-yl]-benzenesulphonamide, m.p. 155° C., was obtained as in Example 1 from the substance prepared in Example 50c.

EXAMPLE 51

4-tert.-Butyl-N-[2-formyl-6-methoxy-5-(2-methoxy-phenyl-sulphanyl)-pyrimidin-4-yl]-benzenesulphonamide MS: M=487, was obtained as in Example 2 from the substance prepared in Example 50.

EXAMPLE 52

4-tert.-Butyl-N-[2-hydroxymethyl-6-methoxy-5-(2-methoxy-phenylsulphanyl)-pyrimidin-4-yl]-benzenesulfonamide, m.p. 152° C., MS: M=490, was obtained as in Example 3 from the substance prepared in Example 51.

EXAMPLE 53

0.145 g of 4-tert.-butyl-N-[5-(2-chloro-5-methoxy-phenoxy)-6-chloromethyl-2-( morpholin-4-yl)-pyrimidin-4-yl]benzenesulphonamide (Example 4) in 3 ml of acetone was added to a sodium phenolate solution from 0,024 g of phenol and 0.06 g of NaOH in 2 ml of acetone and 1 ml of water. The reaction mixture was stirred at 80° C. under argon for 48 hours. Thereafter, the acetone was distilled off and the residue was partitioned between chloroform and water. The chloroform phase was washed with water, dried over sodium sulphate and the solvent was distilled off. The residue was chromatographed over silica gel with chloroform. 0.07 g of 4-tert.-butyl-N-[5-(2-chloro-5-methoxy-phenoxy)-2-morpholin-4-yl-6-phenoxymethyl-pyrimidin-4-yl]benzenesulphonamide, MS: M=639, was obtained.

EXAMPLE 54

N-[6-Biphenyl-4-yloxymethyl-5-(2-chloro-5-methoxy-phenoxy)-2-morpholin-4-yl-pyrimidin-4-yl]-4-tert.-butylbenzenesulphonamide, MS: M=715, was obtained as in Example 53 from sodium 4-biphenolate.

EXAMPLE 55

305 mg of N-[5-(2-chloro-5-methoxy-phenoxy)-6-methoxy-2-methylsulphanyl-pyrimidin-4-yl]-1,3-benzodioxol-5-sulphonamide were obtained from 520 mg of N-[6-chloro-5-methoxy-phenoxy)-2-methylsulphanyl-pyrimidin-4-yl]-1,3-benzodioxol-5-sulphonamide and 270 mg of Na methylate in absolute MeOH as in Example 26. M.p. 176° C. (from ethanol).

EXAMPLE 56

Further examples of compounds obtainable in accordance with the invention are:

4-Methoxy-N-[6-methoxy-5-(2-methoxy-phenoxy)-2,2'-bipyrimidin-4-yl ]-3-(3-morpholin-4-yl-3-oxopropyl)-benzenesulphonamide;

acetic acid 2-[4-[6-methoxy-5-(2-methoxy-phenoxy)-2,2'-bipyrimidin-4-yl-sulphamoyl]phenoxy]-ethyl ester;

4-(2-hydroxy-ethoxy)-N-[6-methoxy-5-(2-methoxy-phenoxy)-2,2'-bipyrimidin-4-yl ]-benzenesulphonamide;

N-[6-methoxy-5-(2-methoxy-phenoxy)-2,2'-bipyrimidin-4-yl]-4-( 2-morpholin-4-yl-2-oxo-ethoxy)-benzenesulphonamide;

N-[6-methoxy-5-(2-methoxy-phenoxy)-2,2'-bipyrimidin-4-yl]-4-(3-morpholin-4-yl-3-oxo-propyl)benzenesulphonamide;

4-methoxy-N-[6-methoxy-5-(2-methoxy-phenoxy)-2,2'-bipyrimidin-4-yl]-3-(2-oxoethyl)-benzenesulphonamide;

[2-methoxy-5-[6-methoxy-5-(2-methoxy-phenoxy)-2,2'-bipyrimidin-4-yl-sulphamoyl]-phenoxy]acetic acid ethyl ester;

4-tert.-butyl-N-[6-methoxy-5-(2-methoxy-phenoxy)-2-methyl-pyrimidin-4-yl ]benzenesulphonamide;

4-tert.-butyl-(6-methoxy-5-naphthalen-1-yloxy-2,2'-bipyrimidin-4-yl)-benzenesuiphonamide.

EXAMPLE A

Tablets containing the following ingredients can be produced in a conventional manner:

| Ingredient | Per tablet |
|---|---|
| Compound of formula I | 10.0–100.0 mg |
| Lactose | 125.0 mg |
| Corn starch | 75.0 mg |
| Talc | 4.0 mg |
| Magnesium stearate | 1.0 mg |

EXAMPLE B

Capsules containing the following ingredients can be produced in a conventional manner:

| Ingredient | Per capsule |
|---|---|
| Compound of formula I | 25.0 mg |
| Lactose | 150.0 mg |
| Corn starch | 20.0 mg |
| Talc | 5.0 mg |

EXAMPLE C

Injection solutions can have the following composition:

| Compound of formula I | 3.0 mg |
|---|---|
| Gelatine | 150.0 mg |
| Phenol | 4.7 mg |
| Water for injection solutions | ad 1.0 ml |

EXAMPLE D 500 mg of compound of formula I are suspended in 3.5 ml of Myglyol 812 and 0.08 g of benzyl alcohol. This suspension is filled into a container having a dosage valve. 5.0 g of Freon 12 under pressure are filled into the container through the valve. The Freon is dissolved in the Myglyol-benzyl alcohol mixture by shaking. This spray container contains about 100 single doses which can be administered individually.

We claim:

1. The method of treating disorders which are associated with endothelin activities, comprising administering to a host in need of such treatment an effective amount of a compound of the formula

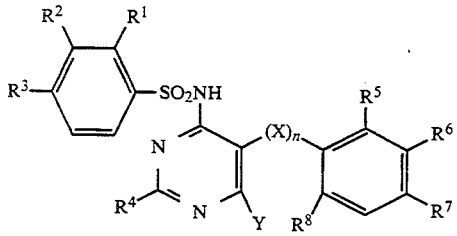

wherein
- $R^1$ is hydrogen, lower-alkyl, lower-alkoxy, lower-alkylthio, halogen or trifluoromethyl;
- $R^2$ is hydrogen, lower-alkyl, halogen, lower-alkoxy, trifluoromethyl or —$OCH_2COOR^9$;
- $R^3$ is hydrogen, lower-alkyl, halogen, lower-alkylthio, trifluoromethyl, lower-alkoxy or trifluoromethoxy;
- $R^2$ and $R^3$ together are butadienyl, methylenedioxy, ethylene-dioxy or isopropylidenedioxy;
- $R^4$ is hydrogen, lower-alkyl, trifluoromethyl, lower-alkoxy, lower-alkylthio, hydroxy-lower-alkyl, hydroxy-lower-alkoxy, hydroxy-lower-alkoxy-lower-alkyl, hydroxy-lower-alkoxy-lower-alkoxy, alkoxy-lower-alkyl, alkoxy-lower-alkyloxy, lower-alkylsulfinyl, lower-alkylsulfonyl, 2-methoxy-3-hydroxypropoxy, 2-hydroxy-3-phenylpropyl, amino-lower-alkyl, lower-alkylamino-lower-alkyl, di-lower-alkylamino-lower-alkyl, amino, lower-alkyl-amino, di-lower-alkylamino, arylamino, aryl, arylthio, aryloxy, aryl-lower-alkyl, heterocyclyl, heterocyclyl-lower-alkyl, heterocyclyl-amino, heterocyclylthio, heterocyclyloxy, —CHO, —$CH_2OH$ or —$CH_2Cl$;
- $R^5$ to $R^8$ are independently hydrogen, halogen, trifluoromethyl, lower-alkoxy, lower-alkylthio or cyano;
- $R^6$ and $R^5$ or $R^7$ together are butadienyl, methylenedioxy, ethylenedioxy or isopropylidenedioxy;
- X is —O— or —S—;
- Y is —CHO, $C_{1-4}$-alkyl, —$(CH_2)_{1-4}$—Z—$R^9$, —$(CH_2)_{1-4}$—OC(O) $(CH_2)_{1-4}CH_3$, —$(CH_2)_{1-4}OC(O)Het$, —$(CH_2)_{1-4}NHC(O)R^{10}$, —$(CH_2)_{1-4}OCH_2CH(OH)CH_2OH$ and cyclic ketals thereof, —$(CH_2)_{1-4}NR^9CH_2CH(OH)CH_2OH$, —$(CH_2)_{1-4}OCH_2CH_2SCH_3$, —$(CH_2)_{1-4}OCH_2CH_2S(O)CH_3$, —$(CH_2)_{1-4}O(CH_2)_{1-4}$-ZH, —$(CH_2)_{1-4}O(CH_2)_{1-4}OC(O)R^{10}$, —$(CH_2)_{1-4}NR^9(CH_2)_{1-4}$-ZH, —$(CH_2)_{1-4}O(CH_2)_{1-4}OC(O)Het$, —$(CH_2)_{0-3}CH(OH)R^{10}$, —$(CH_2)_{0-3}CH(OH)(CH_2)_{1-4}ZH$, —$(CH_2)_{0-3}CH(OH)CH_2SCH_3$, —$(CH_2)_{0-3}CH(OH)CH_2S(O)CH_3$, —$(CH_2)_{0-3}CH(OH)OCH_2CH_2OH$, —$(CH_2)_{0-3}C(O)(CH_2)_{1-4}CH_3$, —$(CH_2)_{0-3}C(O)(CH_2)_{1-4}Z R^{11}$, —$(CH_2)_{0-3}C(O)CH_2Hal$, —$(CH_2)_{1-4}Hal$, —$(CH_2)_{1-4}CN$, —$(CH_2)_{0-3}C(O)OR^9$, —$OR^{12}$ or —$SR^{12}$;
- $R^9$ is hydrogen or $C_{1-4}$-alkyl;
- $R^{10}$ is $C_{1-4}$-alkyl;
- $R^{11}$ is hydrogen, $C_{1-4}$-alkanoyl or heterocyclylcarbonyl;
- $R^{12}$ is $C_{1-4}$-alkyl or —$(CH_2)_{0-4}$-aryl;
- Z is —O—, —S— or —$NR^9$—;

Het is a heterocyclic residue;
Hal is halogen; and
n is 0 or 1;
wherein aryl is phenyl and phenyl substituted with halogen, lower-alkyl, lower-alkoxy, carboxyl or trifluoromethyl and heterocycle is mono- or bicyclic 5- and 6- membered heterocyclic residues which are unsubstituted or which are mono- or di-substituted by lower-alkyl, lower-alkoxy, halogen, aryl or aryl-lower-alkyl and which have oxygen, nitrogen or sulphur as the hetero atom or a salt thereof.

2. A compound of the formula

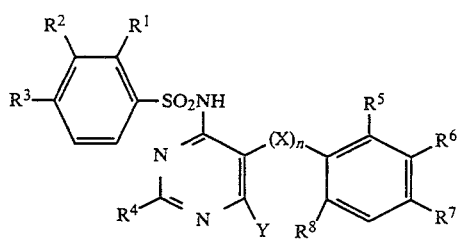

wherein
- $R^1$ is hydrogen, lower-alkyl, lower-alkoxy, lower-alkylthio, halogen or trifluoromethyl;
- $R^2$ is hydrogen, lower-alkyl, halogen, lower-alkoxy, trifluoromethyl or —$OCH_2COOR^9$;
- $R^3$ is hydrogen, lower-alkyl, halogen, lower-alkylthio, trifluoromethyl, lower-alkoxy or trifluoromethoxy;
- $R^2$ and $R^3$ together are butadienyl, methylenedioxy, ethylenedioxy or isopropylidenedioxy;
- $R^4$ is hydrogen, lower-alkyl, trifluoromethyl, lower-alkoxy, lower-alkylthio, hydroxy-lower-alkyl, hydroxy-lower-alkoxy, hydroxy-lower-alkoxy-lower-alkyl, hydroxy-lower-alkoxy-lower-alkoxy, alkoxy-lower-alkyl, alkoxy-lower-alkyloxy, lower-alkylsulfinyl, lower-alkylsulfonyl, 2-methoxy-3-hydroxypropoxy, 2-hydroxy-3-phenylpropyl, amino-lower-alkyl, lower-alkylamino-lower-alkyl, di-lower-alkylamino-lower-alkyl, amino, lower-alkyl-amino, di-lower-alkylamino, arylamino, aryl, arylthio, aryloxy, aryl-lower-alkyl, heterocyclyl, heterocyclyl-lower-alkyl, heterocyclyl-amino, heterocyclylthio, heterocyclyloxy, —CHO, —$CH_2OH$ or —$CH_2Cl$;
- $R^5$ to $R^8$ are independently hydrogen, halogen, trifluoromethyl, lower-alkoxy, lower-alkylthio or cyano;
- $R^6$ and $R^5$ or $R^7$ together are butadienyl, methylenedioxy, ethylenedioxy or isopropylidenedioxy;
- X is —O— or —S—;
- Y is —CHO, $C_{1-4}$-alkyl, —$(CH_2)_{1-4}$—, Z—$R^9$, —$(CH_2)_{1-4}$—OC(O) $(CH_2)_{1-4}CH_3$, —$(CH_2)_{1-4}OC(O)Het$, —$(CH_2)_{1-4}NHC(O) R^{10}$, —$(CH_2)_{1-4}OCH_2CH(OH)CH_2OH$ and cyclic ketals thereof, —$(CH_2)_{1-4}NR^9CH_2CH(OH)CH_2OH$, —$(CH_2)_{1-4}OCH_2CH_2SCH_3$, —$(CH_2)_{1-4}OCH_2CH_2S(O)CH_3$, $(CH_2)_{1-4}O(CH_2)_{1-4}ZH$, —$(CH_2)_{1-4}O(CH_2)_{1-4}OC(O)R^{10}$, —$(CH_2)_{1-4}NR^9(CH_2)_{1-4}$-ZH, —$(CH_2)_{1-4}O(CH_2)_{1-4}OC(O)Het$, —$(CH_2)_{0-3}CH(OH)R^{10}$, —$(CH_2)_{0-3}CH(OH)(CH_2)_{1-4}ZH$, —$(CH_2)_{0-3}CH(OH)CH_2SCH_3$, —$(CH_2)_{0-3}CH(OH)CH_2S(O)CH_3$, —$(CH_2)_{0-3}CH(OH)OCH_2CH_2OH$, —$(CH_2)_{0-3}C(O) (CH_2)_{1-4}CH_3$, —$(CH_2)_{0-3}C(O) (CH_2)_{1-4}Z R^{11}$, —$(CH_2)_{0-3}C-$ (O)CH$_2$Hal, —(CH$_2$)$_{1-4}$Hal, —(CH$_2$)$_{1-4}$CN, —(CH$_2$)$_{0-3}$C(O)OR$^9$, —OR$^{12}$ or —SR$^{12}$;

R$^9$ is hydrogen or C$_{1-4}$-alkyl;

R$^{10}$ is C$_{1-4}$-alkyl;

R$^{11}$ is hydrogen, C$_{1-4}$-alkanoyl or heterocyclylcarbonyl;

R$^{12}$ is C$_{1-4}$-alkyl or —(CH$_2$)$_{0-4}$-aryl;

Z is —O—, —S— or —NR$^9$—;

Het is a heterocyclic residue;

Hal is halogen; and n is 0 or 1;

wherein aryl is phenyl and phenyl substituted with halogen, lower-alkyl, lower-alkoxy, carboxyl, or trifluoromethyl and heterocycle is mono- or bicyclic 5- and 6- membered heterocyclic residues which are unsubstituted or which are mono- or disubstituted by lower-alkyl, lower-alkoxy, halogen, aryl or aryl-lower-alkyl and which have oxygen, nitrogen or sulphur as the hetero atom or a salt thereof.

3. A compound according to claim 1, wherein Y is —OR$^{12}$ or —SR$^{12}$.

4. A compound according to claim 1, wherein Y is —CHO, C$_{1-4}$-alkyl, —(CH$_2$)$_{1-4}$-Z—R$^9$, (CH$_2$)$_{1-4}$-OC(O) (CH$_2$)$_{1-4}$CH$_3$, —(CH$_2$)$_{1-4}$OC(O)Het, —(CH$_2$)$_{1-4}$NHC(O)R$^{10}$, —CH$_2$OCH$_2$CH(OH)CH$_2$OH and cyclic ketals thereof,—CH$_2$NR$^9$CH$_2$CH(OH)CH$_2$OH, —CH$_2$OCH$_2$CH$_2$SCH$_3$, —CH$_2$OCH$_2$CH$_2$S(O)CH$_3$, CH$_2$O(CH$_2$)$_{1-4}$-Z H, —CH$_2$O (CH$_2$)$_{1-4}$OC(O)R$^{10}$, —CH$_2$NR$^9$(CH$_2$)$_{1-4}$Z H, —CH$_2$O (CH$_2$)$_{1-4}$OC(O)Het, —CH$_2$CH(OH)R$^{10}$, —CH$_2$)CH(OH)(CH$_2$)$_{1-4}$Z H, —CH$_2$CH(OH)CH$_2$SCH$_3$, —CH$_2$CH(OH)CH$_2$S(O)CH$_3$, —CH$_2$CH(OH)OCH$_2$CH$_2$OH, —CH$_2$C(O)(CH$_2$)$_{1-4}$CH$_3$, —CH$_2$C(O)(CH$_2$)$_{1-4}$Z R$^{11}$, —C(O)CH$_2$Hal, —CH$_2$Hal,—CH$_2$CN or —C(O)OR$^9$.

5. A compound according to claim 1, wherein n=1 and X=0.

6. A compound according to claim 1, wherein R$^1$ and R$^2$ is hydrogen and R$^3$ is lower-alkyl.

7. A compounds according to claim 1, wherein R$^6$ is lower-alkoxy; R$^5$ and R$^7$ are hydrogen; and R$^8$ is halogen.

8. A compound according to claim 1, wherein R$^4$ is hydrogen, 2-pyrimidinyl, 2- or 3-furyl, 2- or 3-thienyl, p-methoxyphenyl or morpholino.

9. A compound according to claim 4, wherein Y is —CHO, C$_{1-4}$-alkyl, —(CH$_2$)$_{1-4}$—Z—R$_9$, —(CH$_2$)$_{1-4}$NHC(O)R$_{10}$, —CH$_2$OCH$_2$CH(OH)CH$_2$OH and cyclic ketals thereof,—CH$_2$NR$^9$CH$_2$CH(OH)CH$_2$OH, —CH$_2$OCH$_2$CH$_2$S(O)CH$_3$—CH$_2$O(CH$_2$)$_{1-4}$—Z H,—CH$_2$O(CH$_2$)$_{1-4}$OC(O)R$^{10}$, —CH$_2$O ( CH$_2$)$_{1-4}$OC(O)Het or —CH$_2$Hal.

10. A compound of claim 3, selected from the group consisting of:

4-tert-butyl-N-[6-ethoxy-5-(2-methoxyphenoxy)-2,2'-bipyrimidin-4-yl]benzenesulphonamide and 4-tert-butyl-N-[6-methoxy-5-( 2-methoxyphenoxy)-2,2'-bipyrimidin-4-yl]benzenesulphonamide.

11. A compound of claim 4, selected from the group consisting of:

4-tert-butyl-N-[5-( 2-chloro-5-methoxy-phenoxy)-6-methyl-2-(morpholin-4-yl)-pyrimidin-4-yl]-benzenesulphonamide, 4-tert-butyl-N-[5-(2-chloro-5-methoxy-phenoxy)-6-formyl-2(morpholin-4-yl)-pyrimidin-4-yl]-benzenesulphonamide, 4-tert-butyl-N-[5-(2-chloro-5-methoxy-phenoxy)-6-hydroxymethyl-2-( morpholin-4-yl)-pyrimidin-4-yl]benzenesulphonamide, 4-tert-butyl-N-[5-(2-chloro-5-methoxy-phenoxy)-6-chloromethyl-2-(morpholin-4-yl)-pyrimidin-4-yl]benzenesulphonamide, 4-tert-butyl-N-[5-(2-chloro-5-methoxy-phenoxy)-6-( 2-hydroxy-ethoxymethyl)-2-(morpholin-4-yl)-pyrimidin-4-yl]benzenesulphonamide, 4-tert-butyl-N-[5-(2-chloro-5-methoxy-phenoxy)-6-methyl-pyrimidin-4-yl]-benzenesulphonamide, 4-tert-butyl-N-[5-(2-chloro-5-methoxy-phenoxy)-6-formyl-pyrimidin-4-yl]-benzenesulphonamide, 4-tert-butyl-N-[5-(2-chloro-5-methoxy-phenoxy)-6-hydroxymethyl-pyrimidin-4-yl]-benzenesulphonamide, 4-tert-butyl-N-[6-chloromethyl-5-( 2-chloro-5-methoxy-phenoxy)-pyrimidin-4-yl]-benzenesulphonamide, 4-tert-butyl-N-[5-( 2-chloro-5-methoxy-phenoxy)-6-( 2-hydroxy-ethoxy-methyl)-pyrimidin-4-yl]-benzenesulphonamide, thiophene-3-carboxylic acid 2-[6-(4-tert-butylphenylsulphonamino)-5-( 2-chloro-5-methoxy-phenoxy)-2-( morpholin-4-yl)-pyrimidin-4-yl-methoxy]-ethyl ester, (R,S)-4-tert-butyl-N-[5-( 2-chloro-5-methoxy-phenoxy)-6-(2,2-dimethyl- 1,3-dioxolan-4-ylmethoxymethyl)-2-morpholin-4-yl)-pyrimidin-4-yl]-benzenesulphonamide, (R,S)-4-tert-butyl-N-[5-(2-chloro-5-methoxy-phenoxy)-6-(2,3-dihydroxy-propoxymethyl)-2-(morpholin-4-yl)-pyrimidin-4-yl]benzenesulphonamide, 4-tert-butyl-N-[5-( 2-chloro-5-methoxy-phenoxy)-6-( 2-hydroxy-ethylaminomethyl)-pyrimidin-4-yl]-benzenesulphonamide, 4-tert-butyl-N-[5-( 2-chloro-5-methoxy-phenoxy)-6-( 3-hydroxy-propoxymethyl)-pyrimidin-4-yl]-benzenesulphonamide, (RS)-4-tert-butyl-N-[5-(2-chloro-5-methoxy-phenoxy)-6-(2,3-dihydroxypropylaminomethyl)-pyrimidin-4-yl]-benzenesulphonamide, (RS)-4-tert-butyl-N-[5-(2-chloro-5-methoxy-phenoxy)-6-(2,2-dimethyl-1,3-dioxolan-4-ylmethoxymethyl)-pyrimidin-4-yl]benzenesulphonamide, (RS)-4-tert-butyl-N-[5-(2-chloro-5-methoxy-phenoxy)-6-(2,3-dihydroxy-propoxymethyl)-pyrimidin-4-yl]-benzenesulphonamide, pyridin-3-ylacetic acid 2-[6-(4-tert-butyl-phenylsulphonyl-amino)-5-(2-chloro-5-methoxy-phenoxy)-pyrimidin-4-ylmethoxy]ethyl ester, pyridin-4-ylacetic acid 2-[6-(4-tert-butyl-phenylsulphonyl-amino)-5-(2-chloro-5-methoxy-phenoxy)-pyrimidin-4-ylmethoxy]ethyl ester, furan-3-carboxylic acid 2-[6-(4-tert-butyl-phenylsulphonyl-amino)-5-(2-chloro-5-methoxy-phenoxy)-pyrimidin-4-ylmethoxy]ethyl ester, thiophene-3-carboxylic 2-[6-(4-tert-butyl-phenylsulphonyl-amino)-5-(2-chloro-5-methoxy-phenoxy)-pyrimidin-4-ylmethoxy]ethyl ester and ethyl 6-(4-tert-butyl-phenylsulphonyl-amino)-2-chloro-5-phenoxy-pyrimidin-3-carboxylate.

12. A compound of claim 1, selected from the group consisting of:

4-tert-butyl-N-[5-(2-chloro-5-methoxy-phenoxy)-6-methyl-2,2'-bipyrimidinyl-4-yl]-benzenesulphonamide, (S)-4-tert.-butyl-N-[5-(2-chloro-5-methoxy-phenoxy)-6-(2,2-dimethyl- 1,3-dioxolan-4-ylmethoxymethyl)-2-morpholin-4-yl)-pyrimidin-4-yl]-benzenesulphonamide, (R)-4-tert.-butyl-N-[5-(2-chloro-5-methoxy-phenoxy)-6-(2,2-dimethyl-1,3-dioxolan-4-ylmethoxymethyl)-2-(morpholin-4-yl)-pyrimidin-4-yl]-benzenesulphonamide, (S)-4-tert.-butyl-N-[5-(2-chloro-4-methoxy-phenoxy)-6-(2,3-dihydroxypropoxymethyl)-2-(morpholin-4-yl)-pyrimidin-4-yl]benzenesulphonamide, (R)-4-tert.-butyl-N-[5-(2-chloro-5-methoxy-phenoxy)-6-(2,3-dihydroxy-propoxymethyl)-2-(morpholin-4-yl)-pyrimidin-4-yl-benzenesulphonamide, (4S,5S)-4-tert.-butyl-N-[5-(2-chloro-5-methoxy-phenoxy)-6-(5-hydroxymethyl-2,2-dimethyl- 1,3-dioxolan-4-ylmethoxymethyl)-pyrimidin-4-yl]-benzenesulphonamide, (2S,3S)-4-tert.-butyl-N-[5-(2-chloro-5-methoxy-phenoxy)-6(2,3,4-trihydroxybutoxymethyl)-4-yl]benzbenzenesulphonamide, 6-(4-tert.-butyl-phenylsulphonamino )-5-( 2-chloro-5-methoxy-phenoxy)-2,2'-bipyrimidinyl-4-carboxaldehyde, 4-tert.-butyl-N-[5-(2-chloro-5-methoxy-phenoxy)-6-hydroxymethyl-2,2'-bipyrimidin-4-yl]-benzenesulphonamide, 4-tert.-butyl-N-[5-(2-chloro-5-methoxy-phenoxy)-6-chloromethyl-2,2'-bipyrimidin-4-yl]-benzenesulphonamide, 4-tert.-butyl-N-[5-( 2-chloro-5-methoxy-phenoxy)-6-( 2-hydroxy-ethoxymethyl)-2-2'-bipyrimidin-4-yl]benzenesulphonamide, 4-tert.-butyl-N-[5-(2-chloro-5-methoxy-phenoxy)-6-methoxy-2-methyl-pyrimidin-4-yl]-benzenesulphonamide, 4-tert.-butyl-N-[5-( 2-chloro-5-methoxy-phenoxy)-2-formyl-6-methoxypyrimidin-4-yl]-benzenesulphonamide, 4-tert.-butyl-N-[5-( 2-chloro-5-methoxy-phenoxy)-2-hydroxymethyl-6-methoxy-pyrimidin-4-yl]-benzenesulphonamide, 4-tert.-butyl-N-[5-( 2-chloro-5-methoxy-phenoxy)-2-chloromethyl-6-methoxy-pyrimidin-4-yl]-benzenesulphonamide, 4-tert.-butyl-N-[5-( 2-chloro-5-methoxy-phenoxy)-2-( 2-hydroxy-ethoxymethyl-6-methoxy-pyrimidin-4-yl]benzenesulphonamide, (RS)-4-tert.-butyl-N-[5-( 2-chloro-5-methoxy-phenoxy)-2(2,2-dimethyl-1,3-dioxolan-4-ylmethoxy-methyl)-6-methoxy-pyrimidin-4-yl]-benzenesulphonamide, (RS)-4-tert.-butyl-N-[5-( 2-chloro-5-methoxy-phenoxy)-2(2,3-dihydroxy-propoxy-methyl)-6-methoxy-pyrimidin-4-yl]benzenesulphonamide, 4-tert.-butyl-N-[5-(2-chloro-5-methoxy-phenoxy)-2-aminomethyl-6-methoxy-pyrimidin-4-yl]-benzenesulphonamide, N-[5-(2-chloro-5-methoxy-phenoxy)-6-( 2-methoxy-ethoxy)-2-methyl-pyrimidin-4-yl]-1,3-benzodioxol-5-sulphonamide, N-[5-(2-chloro-5-methoxy-phenoxy)-2-formyl-6-(2-methoxy-ethoxy)-pyrimidin-4-yl]- 1,3-benzodioxol-5-sulphonamide, N-[5-(2-chloro-5-methoxy-phenoxy)-2-hydroxymethyl-6-(2-methoxy-ethoxy)-pyrimidin-4-yl]-1,3-benzodioxol-5-sulphonamide, N-[5-(2-chloro-5-methoxy-phenoxy)-2-chloromethyl-6-( 2-methoxy-ethoxy)-pyrimidin-4-yl]- 1,3-benzodioxol-5-sulphonamide, N-[5-(2-chloro-5-methoxy-phenoxy)-2-(2-hydroxy-ethoxymethyl)-6-( 2-methoxy-ethoxy)-pyrimidin-4-yl]- 1,3-benzodioxol-5-sulphonamide, 4-tert.-butyl-N-[6-methoxy-5-( 2-methoxy-phenylsulphanyl)-methyl-pyrimidin-4-yl]-benzenesulphonamide, 4-tert.-butyl-N-[2-formyl-6-methoxy-5-(2-methoxy-phenylsulfanyl)-pyrimidin-4-yl]-benzenesulphonamide and 4-tert.-butyl-N-[2-hydroxymethyl-6-methoxy-5-(2-methoxy-phenylsulfanyl)-pyrimidin-4-yl]-benzenesulphonamide.

13. A pharmaceutical composition comprising an effective amount of a compound of the formula $$\begin{array}{c}
R^2 \quad R^1 \\
R^3 \longrightarrow \text{—SO}_2\text{NH} \\
\quad \quad \quad \quad N \quad (X)_n \quad R^5 \\
R^4 \quad N \quad Y \quad R^8 \quad R^6 \\
\quad \quad \quad \quad \quad \quad \quad \quad R^7
\end{array} \quad I$$

wherein $R^1$ is hydrogen, lower-alkyl, lower-alkoxy, lower-alkylthio, halogen or trifluoromethyl;

$R^2$ is hydrogen, lower-alkyl, halogen, lower-alkoxy, trifluoromethyl or —OCH$_2$COOR$^9$;

$R^3$ is hydrogen, lower-alkyl, halogen, lower-alkylthio, trifluoromethyl, lower-alkoxy or trifluoromethoxy;

$R^2$ and $R^3$ together are butadienyl, methylenedioxy, ethylene-dioxy or isopropylidenedioxy;

$R^4$ is hydrogen, lower-alkyl, trifluoromethyl, lower-alkoxy, lower-alkylthio, hydroxy-lower-alkyl, hydroxy-lower-alkoxy, hydroxy-lower-alkoxy-lower-alkyl, hydroxy-lower-alkoxy-lower alkoxy, alkoxy-lower-alkyl, alkoxy-lower-alkyloxy, lower-alkylsulfinyl, lower-alkylsulfonyl, 2-methoxy-3-hydroxypropoxy, 2-hydroxy-3-phenylpropyl, amino-lower-alkyl, lower-alkylamino-lower-alkyl, di-lower-alkylamino-lower-alkyl, amino, lower-alkyl-amino, di-lower-alkylamino, arylamino, aryl, arylthio, aryloxy, aryl-lower-alkyl, heterocyclyl, heterocyclyl-lower-alkyl, heterocyclyl-amino, heterocyclylthio, heterocyclyloxy, —CHO, —CH$_2$OH or —CH$_2$Cl;

$R^5$ to $R^8$ are independently hydrogen, halogen, trifluoromethyl, lower-alkoxy, lower-alkylthio or cyano;

$R^6$ and $R^5$ or $R^7$ together are butadienyl, methylenedioxy, ethylenedioxy or isopropylidenedioxy;

X is —O— or —S—;

Y is —CHO, C$_{1-4}$-alkyl, —(CH$_2$)$_{1-4}$-Z—R$^9$, —(CH$_2$)$_{1-4}$—OC(O)(CH$_2$)$_{1-4}$CH$_3$, —(CH$_2$)$_{1-4}$OC(O)Het, —(CH$_2$)$_{1-4}$NHC(O)R$^{10}$, —(CH$_2$)$_{1-4}$OCH$_2$CH (OH) CH$_2$OH and cyclic ketals thereof, —(CH$_2$)$_{1-4}$NR$^9$CH$_2$CH(OH)CH$_2$OH, —(CH$_2$)$_{1-4}$OCH$_2$CH$_2$SCH$_3$, —(CH$_2$)$_{1-4}$OCH$_2$CH$_2$S(O)CH$_3$, —(CH$_2$)$_{1-4}$O(CH$_2$)$_{1-4}$-ZH, —(CH$_2$)$_{1-4}$O(CH$_2$)$_{1-4}$OC(O)R$^{10}$, —(CH$_2$)$_{1-4}$NR$^9$(CH$_2$)$_{1-4}$-ZH, —(CH$_2$)$_{1-4}$O(CH$_2$)$_{1-4}$OC(O)Het, —(CH$_2$)$_{0-3}$CH(OH)R$^{10}$, —(CH$_2$) —(CH$_2$)$_{0-3}$CH(OH)(CH$_2$)$_{1-4}$ZH, —(CH$_2$)$_{0-3}$CH(OH)CH$_2$SCH$_3$, —(CH$_2$)$_{0-3}$CH(OH)CH$_2$S(O)CH$_3$, —(CH$_2$)$_{0-3}$CH(OH)OCH$_2$CH$_2$OH, —(CH$_2$)$_{0-3}$C(O)(CH$_2$)$_{1-4}$CH$_3$, —(CH$_2$)$_{0-3}$C(O)(CH$_2$)$_{1-4}$Z R$^{11}$, —(CH$_2$)$_{0-3}$C(O)CH$_2$Hal, —(CH$_2$)$_{1-4}$Hal, —(CH$_2$)$_{1-4}$CN, —(CH$_2$)$_{0-3}$C(O)OR$^9$, —OR$^{12}$ or —SR$^{12}$;

R$^9$ is hydrogen or C$_{1-4}$-alkyl;

R$^{10}$ is C$_{1-4}$-alkyl;

R$^{11}$ is hydrogen, C$_{1-4}$-alkanoyl or heterocyclylcarbonyl;

R$^{12}$ is C$_{1-4}$-alkyl or —(CH$_2$)$_{0-4}$-aryl;

Z is —O—, —S— or —NR$^9$—;

Het is a heterocyclic residue;

Hal is halogen; and n is 0 or 1;

wherein aryl is phenyl and phenyl substituted with halogen, lower-alkyl, lower-alkoxy, carboxyl or trifluoromethyl and heterocycle is mono- or bicyclic 5- and 6- membered heterocyclic residues which are unsubstituted or which are mono- or di-substituted by lower-alkyl, lower-alkoxy, halogen, aryl or aryl-lower-alkyl and which have oxygen, nitrogen or sulphur as the hetero atom or a salt thereof and a pharmaceutical carrier material.

14. A process for the manufacture of a compound of the formula

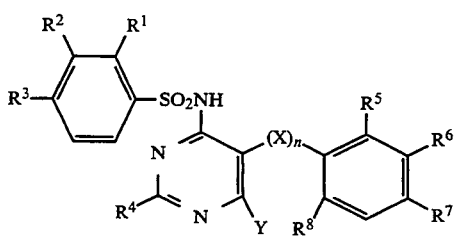

I wherein

R$^1$ is hydrogen, lower-alkyl, lower-alkoxy, lower-alkylthio, halogen or trifluoromethyl;

R$^2$ is hydrogen, lower-alkyl, halogen, lower-alkoxy, trifluoromethyl or —OCH$_2$COOR$^9$;

R$^3$ is hydrogen, lower-alkyl, halogen, lower-alkylthio, trifluoromethyl, lower-alkoxy or trifluoromethoxy;

R$^2$ and R$^3$ together are butadienyl, methylenedioxy, ethylenedioxy or isopropylidenedioxy;

R$^4$ is hydrogen, lower-alkyl, trifluoromethyl, lower-alkoxy, lower-alkylthio, hydroxy-lower-alkyl, hydroxy-lower-alkoxy, hydroxy-lower-alkoxy-lower-alkyl, hydroxy-lower-alkoxy-lower-alkoxy, alkoxy-lower-alkyl, alkoxy-lower-alkyloxy, lower-alkylsulfinyl, lower-alkylsulfonyl, 2-methoxy-3-hydroxypropoxy, 2-hydroxy-3-phenylpropyl, amino-lower-alkyl, lower-alkylamino-lower-alkyl, di-lower-alkylamino-lower-alkyl, amino, lower-alkyl-amino, di-lower-alkylamino, arylamino, aryl, arylthio, aryloxy, aryl-lower-alkyl, heterocyclyl, heterocyclyl-lower-alkyl, heterocyclyl-amino, heterocyclylthio, heterocyclyloxy, —CHO, —CH$_2$OH or —CH$_2$Cl;

R$^5$ to R$^8$ are independently hydrogen, halogen, trifluoro-methyl, lower-alkoxy, lower-alkylthio or cyano;

R$^6$ and R$^5$ or R$^7$ together are butadienyl, methylenedioxy, ethylenedioxy or isopropylidenedioxy;

X is —O— or —S—;

Y is —CHO, C$_{1-4}$-alkyl, —(CH$_2$)$_{1-4}$-Z—R$^9$, —(CH$_2$)$_{1-4}$—OC(O)(CH$_2$)$_{1-4}$CH$_3$, —(CH$_2$)$_{1-4}$OC(O)Het, —(CH$_2$)$_{1-4}$NHC(O) R$^{10}$, —(CH$_2$)$_{1-4}$OCH$_2$CH(OH)CH$_2$OH and cyclic ketals thereof, —(CH$_2$)$_{1-4}$NR$^9$CH$_2$CH(OH)CH$_2$OH, —(CH$_2$)$_{1-4}$OCH$_2$CH$_2$SCH$_3$, —(CH$_2$)$_{1-4}$OCH$_2$CH$_2$S(O)CH$_3$, —(CH$_2$)$_{1-4}$O(CH$_2$)$_{1-4}$-ZH, —(CH$_2$)$_{1-4}$O(CH$_2$)$_{1-4}$OC(O)R$^{10}$, —(CH$_2$)$_{1-4}$NR$^9$(CH$_2$)$_{1-4}$-ZH, —(CH$_2$)$_{1-4}$O(CH$_2$)$_{1-4}$OC(O)Het, —(CH$_2$)$_{0-3}$CH(OH)R$^{10}$, —(CH$_2$)$_{0-3}$CH(OH) (CH$_2$)$_{1-4}$ZH, —(CH$_2$)$_{0-3}$CH(OH)CH$_2$SCH$_3$, —(CH$_2$)$_{0-3}$CH(OH)CH$_2$S(O)CH$_3$, —(CH$_2$)$_{0-3}$CH(OH)OCH$_2$CH$_2$OH, —(CH$_2$)$_{0-3}$C(O)(CH$_2$)$_{1-4}$CH$_3$, —(CH$_2$)$_{0-3}$C(O)(CH$_2$)$_{1-4}$Z R$^{11}$, —(CH$_2$)$_{0-3}$C(O)CH$_2$Hal, —(CH$_2$)$_{1-4}$Hal, —(CH$_2$)$_{1-4}$CN, —(CH$_2$)$_{0-3}$C(O)OR$^9$, —OR$^{12}$ or —SR$^{12}$;

R$^9$ is hydrogen or C$_{1-4}$-alkyl;

R$^{10}$ is C$_{1-4}$-alkyl;

R$^{11}$ is hydrogen, C$_{1-4}$-alkanoyl or heterocyclylcarbonyl;

R$^{12}$ is C$_{1-4}$-alkyl or —(CH$_2$)$_{0-4}$-aryl;

Z is —O—, —S— or —NR$^9$—;

Het is a heterocyclic residue;

Hal is halogen; and n is 0 or 1;

wherein aryl is phenyl and phenyl substituted with halogen, lower-alkyl, lower-alkoxy, carboxyl or trifluoromethyl and heterocycle is mono- or bicyclic 5- and 6- membered heterocyclic residues which are unsubstituted or which are mono- or di-substituted by lower-alkyl, lower-alkoxy, halogen, aryl or aryl-lower-alkyl and which have oxygen, nitrogen or sulphur as the hetero atom or a salt thereof which process comprises a) reacting a compound of the formula

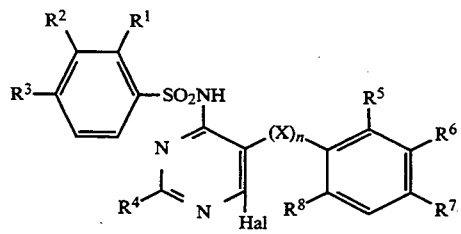

II wherein R$^1$-R$^8$, X and n have the significance given earlier in this claim and Hal is halogen, with a compound of the formula

R$^{12}$AM     III wherein A is oxygen or sulphur and M is an alkali metal, to give a compound of formula I in which Y is the residue —OR$^{12}$ or —SR$^{12}$; or b) reacting a compound of the formula

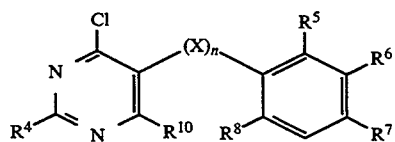

IV wherein R$^4$-R$^8$, R$^{10}$, X and n have the significance given earlier in this claim, with a compound of the formula

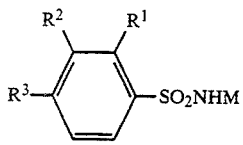 V wherein $R^1$, $R^2$, $R^3$ and M have the significance given earlier
in this claim, to give a compound of formula I in which Y is a residue $R^{10}$ and $R^1$-$R^8$, X and n have the significance given above, if desired, oxidizing a compound of formula I obtained in which Y and/or $R^4$ is a residue $CH_3$ to give a compound of formula I in which Y and/or $R^4$ is a residue CHO and, if desired, converting the residue CHO into a different residue Y and/or $R^4$; or c) reacting a compound of the formula

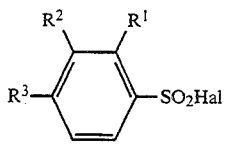 VI wherein $R^1$, $R^2$, $R^3$ and Hal has the significance given earlier in this claim, with a compound of the formula

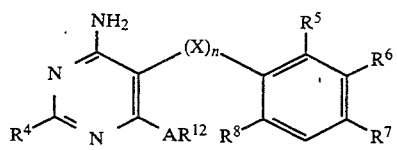 VII wherein $R^4$-$R^8$, $R^{12}$, n, A and X have the significance given
earlier in this claim, and, if desired, converting the compound of formula I obtained into a salt.

* * * * *